United States Patent
Wietgrefe

(10) Patent No.: US 8,641,910 B2
(45) Date of Patent: Feb. 4, 2014

(54) SYSTEMS AND PROCESSES FOR PRODUCING BIOFUELS FROM BIOMASS

(75) Inventor: Gary Wietgrefe, Sioux Falls, SD (US)

(73) Assignee: Syngenta Participations AG, Basel (CH)

( * ) Notice: Subject to any disclaimer, the term of this patent is extended or adjusted under 35 U.S.C. 154(b) by 528 days.

(21) Appl. No.: 12/866,134

(22) PCT Filed: Feb. 3, 2009

(86) PCT No.: PCT/US2009/032909
§ 371 (c)(1),
(2), (4) Date: Sep. 1, 2010

(87) PCT Pub. No.: WO2009/100042
PCT Pub. Date: Aug. 13, 2009

(65) Prior Publication Data
US 2010/0319424 A1     Dec. 23, 2010

Related U.S. Application Data

(60) Provisional application No. 61/063,626, filed on Feb. 5, 2008.

(51) Int. Cl.
*B01D 11/04* (2006.01)
*B01D 11/02* (2006.01)
*C10L 5/04* (2006.01)

(52) U.S. Cl.
USPC ............. 210/773; 210/634; 210/768; 44/605; 426/7; 426/49

(58) Field of Classification Search
None
See application file for complete search history.

(56) References Cited

U.S. PATENT DOCUMENTS

| | | | |
|---|---|---|---|
| 5,196,636 A | 3/1993 | Sohndahl | |
| 5,597,558 A | 1/1997 | Aubert et al. | |
| 6,108,967 A | 8/2000 | Erickson | |
| 6,355,456 B1 | 3/2002 | Hallberg et al. | |
| 2003/0024686 A1 | 2/2003 | Ouellette | |
| 2007/0031953 A1 | 2/2007 | Dunson et al. | |
| 2007/0224669 A1* | 9/2007 | Jewell | 435/167 |
| 2007/0244719 A1 | 10/2007 | David | |
| 2007/0300324 A1 | 12/2007 | Nadel et al. | |
| 2008/0009047 A1 | 1/2008 | Bell et al. | |
| 2008/0009055 A1 | 1/2008 | Lewnard | |

OTHER PUBLICATIONS

Valva et al. Evaluation of sugar content in corn stalks (*Zea mays* L.) for alcohol production. Maydica XXV (1980) 185-197.*

(Continued)

*Primary Examiner* — Katherine Zalasky
(74) *Attorney, Agent, or Firm* — Dale W. Skalla

(57) ABSTRACT

Systems and processes for converting bulky lignocellulosic biomass to high density biomass products, including biofuels, are described. The systems and processes relate to treating freshly harvested plant materials, generally at or in close proximity to sites where the plant materials are harvested, to effect saccharification, alcoholic fermentation, or simultaneous saccharification and fermentation, thereby providing a liquefied biomass. The liquefied biomass is extracted to provide liquid extracts comprising biomass-derived water and water soluble biomass saccharification and fermentation products, including fermentable sugars and alcohols. The liquid biomass extracts can be transported via pipeline to other locations for fermentation, further saccharification, and/or purification to provide biofuel. Alternatively, the liquefied biomass can be used to prepare a biomass slurry that can be transported via pipeline.

25 Claims, 2 Drawing Sheets

(56) References Cited

OTHER PUBLICATIONS

Sharma et al., "Optimization of fermentation parameters to production of ethanol from kinnow waste and banana peels by simultaneous saccharification and fermentation", Indian J. Microbiol., (Dec. 2007) vol. 47, pp. 310-312.

New Energy Symposium—Event Overview of Third Annual New Energy Symposium, Jul. 9-10, 2008, Albany NanoTech Complex, Albany, NY; hosted by New Energy New York and the College of Nanoscale Science and Engineering, downloaded from Internet Nov. 18, 2010.

Horton, Jerry, (founder, SweetWater Ethanol, LLC) "Business Case Element," presentation from Third Annual New Energy Symposium, Jul. 9-10, 2008, Albany NanoTech Complex, Albany, NY; hosted by New Energy New York and the College of Nanoscale Science and Engineering.

Horton, Jerry, (founder, SweetWater Ethanol, LLC) "Making Ethanol Make Sense," presentation from Third Annual New Energy Symposium, Jul. 9-10, 2008, Albany NanoTech Complex, Albany, NY; hosted by New Energy New York and the College of Nanoscale Science and Engineering.

* cited by examiner

SYSTEMS AND PROCESSES FOR PRODUCING BIOFUELS FROM BIOMASS

CROSS-REFERENCE TO RELATED APPLICATIONS

This application claims the benefit of U.S. Provisional Patent Application Ser. No. 61/063,626, filed Feb. 5, 2008; the disclosure of which is incorporated herein by reference in its entirety.

TECHNICAL FIELD

The presently disclosed subject matter provides processes for converting lignocellulosic biomass to liquid biomass extracts and to biofuels, such as bioethanol, ethanol/gasoline blends and other bioalcohols. Also provided is a system for converting biomass to biofuel, the system comprising a liquid biomass extract treatment facility and a pipeline network comprising one or more pipelines for transporting liquid biomass extract from one or more remote liquid biomass extract production sites to the treatment facility.

ABBREVIATIONS

° C.=degree Celsius
ADF=acid detergent fiber
ASTM=American Society of Testing and Materials
cm=centimeter
$CO_2$=carbon dioxide
DM=dry matter
DMF=dimethylfuran
EtOH=ethanol
FPU=filter paper units
FTIR=Fourier-Transform infrared
HPLC=high-performance liquid chromatography
mly=million liters per year
NDS=neutral detergent fiber
NIRS=near-infrared spectroscopy
$O_2$=oxygen gas
SSF=simultaneous saccharification and fermentation
TAPPI=Technical Association of the Pulp and Paper Industry, Inc.
TLC=theoretical length of cut
WSC=water soluble carbohydrate

BACKGROUND

Cellulosic and lignocellulosic feedstocks (e.g., plant-derived biomass) provide a large renewable source of potential starting materials for the production of a variety of chemicals, plastics, fuels and feeds. For example, biomass feedstocks comprise a variety of carbohydrates which can be hydrolyzed to provide fermentable sugars for use in the production of alcohol fuels, such as ethanol, methanol, and butanol.

The use of biomass feedstocks for production of biofuels is motivated by both economic and environmental concerns, including reduction of greenhouse gas emissions, enhancement of the fuel supply, and maintenance of the rural economy. Energy legislation enacted in 2007 in the United States provides that yearly ethanol production reach 136.3 billion liters by the year 2022, with at least 79.5 billion liters coming from lignocellulosic feedstocks, such as corn stover, prairie grass, and poplar trees, as opposed to corn grain, which comprises a high amount of more easily hydrolyzed starch. See, e.g., *Ethanol Producer Magazine*, December 2007.

For recent reviews concerning biomass-to-ethanol conversion strategies see DiPardo, *Journal of Outlook for Biomass Ethanol Production and Demand* (EIA Forecasts), 2002; and Lynd, et al., *Current Opinion in Biotechnology*, 16, 577-583 (2005). The conversion of biomass to ethanol can involve significant amounts of water and energy, particularly in saccharification steps. Due to the complex structure of cellulosic and lignocellulosic materials, some form of chemical, thermal, mechanical, or enzymatic pretreatment is generally needed to increase saccharification of the carbohydrates. See Chen, Y., et al., *Appl. Biochem. Biotechnol.* 143, 80-92 (2007). Further, raw biomass tends to be bulky, but can lose significant value if exposed to the weather, thus necessitating large weather-proof biomass storage facilities. Still another significant obstacle for converting biomass into ethanol or other biofuels is the cost involved in transporting large volumes of the relatively low density biomass to centralized biofuel production facilities for processing. For a discussion of the costs associated with trucking various biomass materials, see Kumar et al., *Bioresource Technology*, 96, 819-829 (2005).

Thus, there is a continuing need for improved processes and systems for converting biomass to biofuels and/or high density biofuel feedstocks. In particular, there is a need for efficient processes that can reduce biomass storage and transport issues, and which do not require the use of large amounts of externally provided water.

SUMMARY

In some embodiments, the presently disclosed subject matter provides a process for converting biomass to a liquid biomass extract comprising fermentable sugars; the process comprising:
  providing biomass, wherein providing the biomass comprises harvesting a plant material, wherein the harvesting is timed to provide a plant material comprising a moisture content of between about 70% and about 95%;
  placing the biomass into an atmospherically controlled chamber for a period of time and under suitable conditions to effect saccharification of the biomass, alcohol fermentation of the biomass, or combinations thereof, thereby providing a liquefied biomass, wherein the liquefied biomass comprises residual solids, biomass-derived water, and water-soluble products, the water soluble products comprising fermentable sugars or fermentable sugars and an alcohol; and
  serially extracting the liquefied biomass, wherein serially extracting the liquefied biomass comprises:
    removing a first portion of the liquefied biomass from the chamber prior to significant degradation of the fermentable sugars to acid fermentation products;
    collecting at least a portion of the biomass-derived water and water soluble products from the first portion of the liquefied biomass; and
    repeating the removing and collecting for one or more additional portions of the liquefied biomass; thereby providing a liquid biomass extract and a residual solids fraction.

In some embodiments, providing the biomass further comprises chopping the biomass. In some embodiments, the chopping comprises chopping the biomass to a theoretical length of cut (TLC) between about 0.3 and about 1.3 centimeters.

In some embodiments, the suitable conditions further comprise providing an inoculant comprising one or more biomass-processing biocatalyst. In some embodiments, the inoculant is added to the biomass prior to or during placing the biomass into the atmospherically controlled chamber. In some embodiments, the biomass-processing biocatalyst comprises one or more of a lignocellulose-processing enzyme and an alcohol-producing microbe.

In some embodiments, the inoculant further comprises one or more additive selected from the group consisting of a biocatalyst nutrient, a biocatalyst growth factor, a pH-adjusting agent, an electrolyte, a nitrogen-containing chemical, an antimicrobial agent, an oxygen-depleting agent, a beneficial microbe, a plasticizer, a softener, and combinations thereof. In some embodiments, the oxygen-depleting agent is selected from the group consisting of $CO_2$ gas and chloropicrin. In some embodiments, the nitrogen-containing chemical is selected from the group consisting of ammonia, ammonium chloride, urea, ammonium nitrate, and ammonium phosphate.

In some embodiments, the process further comprises monitoring contents of the atmospherically controlled chamber at one or more locations in the chamber to determine one or more of the pH, temperature, oxygen gas content, escaping gases, microbial activity, enzymatic activity, % dry matter (DM) conversion, % of theoretical sugars converted, fermentable sugars concentration, alcohol concentration, plant material-derived acid concentration, and microbial nutrient concentration. In some embodiments, conditions in the atmospherically controlled chamber are adjusted during the period of time to alter one or more of pH, temperature, oxygen gas content, microbial activity, enzymatic activity, and microbial nutrient content.

In some embodiments, the plant material is derived from a plant selected from one or more of the group consisting of maize, soybean, millet, milo, rye, wheat, triticale, oats, barley, rice, sorghum, sudangrass, switchgrass, *Miscanthus*, alfalfa, cotton, sisal, hemp, jute, turf grass, rape, sunflower, willow, eucalyptus, poplar, pine, willow, tobacco, clover, bamboo, flax, pea, radish, turnip, potato, sweet potato, cassava, taro, beet, sugar beet, sugar cane, and canola. In some embodiments, the biomass comprises one or more of the group consisting of whole plant corn, corn stover, corn cobs, and soybean forage. In some embodiments, the harvesting is timed to provide a plant material comprising a moisture content of about 75% or more.

In some embodiments, the biomass comprises plant material selected based on one or more characteristic of the group consisting of sugar content, cellulose content, lignin content, cost, growing season, drought resistance, disease resistance, individual plant size, and tonnage. In some embodiments, the biomass comprises plant material from a male-sterile, tropical hybrid corn plant.

In some embodiments, at least a portion of the plant material is derived from a transgenic plant. In some embodiments, the transgenic plant comprises one or more lignocellulose-processing enzyme. In some embodiments, the lignocellulose-processing enzyme is an amylase.

In some embodiments, the atmospherically controlled chamber is an upright silo.

In some embodiments, the period of time is from about 20 hours to about 21 days. In some embodiments, the period of time is from about 24 hours to about 72 hours.

In some embodiments, the collecting comprises one or more of centrifuging, pressing, and decanting. In some embodiments, the liquid biomass extract comprises water soluble products and at least about 80% of the biomass-derived water from the first portion and the one or more additional portions of the liquefied biomass, and the residual solids fraction comprises the residual solids and about 20% of the biomass-derived water from the first portion and the one or more additional portions of the liquefied biomass.

In some embodiments, the plant material is harvested at a first location and the atmospherically controlled chamber is at a location at or in close proximity to the first location. In some embodiments, the process further comprises transporting the liquid biomass extract to a second location; and treating the liquid biomass extract to provide a biofuel. In some embodiments, the second location is an ethanol plant. In some embodiments, one or more of pH, enzymatic activity level, microbial activity level, and viscosity of the liquid biomass extract is adjusted prior to the transporting.

In some embodiments, the transporting comprises piping the liquid biomass extract. In some embodiments, the transporting comprises piping the liquid biomass extract for at least about 8 kilometers. In some embodiments, the transporting comprises piping the liquid biomass extract for at least about 80 kilometers. In some embodiments, the transporting comprises piping the liquid biomass extract for at least about 160 kilometers.

In some embodiments, treating the liquid biomass extract comprises one or more of fermenting fermentable sugars in the liquid biomass extract and purifying the liquid biomass extract to provide a purified alcohol. In some embodiments, the treating further comprises saccharifying water soluble carbohydrates in the liquid biomass extract. In some embodiments, purifying the liquid biomass extract to provide a purified alcohol comprises separating alcohol from biomass-derived water by one or more of distilling and drying over molecular sieves. In some embodiments, the purified alcohol is mixed with gasoline to provide the biofuel.

In some embodiments, the process further comprises treating the residual solids fraction to provide one or more co-products selected from the group consisting of an animal feed, a fertilizer, methanol, and a boiler fuel. In some embodiments, the process further comprises collecting the biomass-derived water from the liquid biomass extract and using the biomass-derived water for one or more of irrigating a biomass plant material prior to harvesting, diluting the biomass or liquid biomass extract for saccharification, fermentation, or saccharification and fermentation, processing of the residual solids fraction, and distilling a biofuel.

In some embodiments, providing biomass further comprises freezing the biomass to control endogenous microbes, to break down lignocellulosic materials within the biomass, or combinations thereof.

In some embodiments, conditions within the atmospherically controlled chamber comprise heat generated by one or more of plant cell respiration, microbial activity, and enzymatic activity. In some embodiments, the heat generated by one or more of plant cell respiration, microbial activity, and enzymatic activity is controlled by one or more of biomass moisture, ambient harvest temperature, biomass theoretical length of cut (TLC), oxygen content of the atmospherically controlled chamber, nutrients, pH, inoculant load, inoculant type, and a heat exchange system. In some embodiments, the heat generated by one or more of plant cell respiration, microbial activity, and enzymatic activity provides the liquefied biomass in the absence of additional heat.

In some embodiments, the presently disclosed subject matter provides a process for converting biomass to biofuel, the process comprising:

providing biomass, wherein providing the biomass comprises harvesting a plant material at a first location wherein the harvesting of the plant material is timed to provide a plant material comprising a moisture content of between about 70% and about 95%;

placing the biomass into an atmospherically controlled chamber at or in close proximity to the first location for a period of time and under suitable conditions to effect saccharification of the biomass, alcohol fermentation of the biomass, or a combination thereof, thereby providing a liquefied biomass, wherein the liquefied biomass comprises residual solids, biomass-derived water, and water-soluble products, the water soluble products comprising one or more of fermentable sugars and an alcohol;

extracting at least a portion of the biomass-derived water and the water-soluble products from the liquefied biomass, thereby providing a liquid biomass extract and a residual solids fraction;

transporting the liquid biomass extract to a second location; and treating the liquid biomass extract; thereby providing the biofuel.

In some embodiments, the alcohol is ethanol and the biofuel comprises ethanol. In some embodiments, the harvesting of the plant material is timed to provide plant material comprising a moisture content of about 75% or greater.

In some embodiments, placing the biomass into an atmospherically controlled chamber at or in close proximity to the first location for a period of time and under suitable conditions to effect saccharification of the biomass, alcohol fermentation of the biomass, or a combination thereof, thereby providing a liquefied biomass, comprises: filling the atmospherically controlled chamber with the biomass; and monitoring one or more of the group consisting of temperature, atmospheric oxygen level, escaping gases, pH, production of saccharification products, production of alcohol fermentation products, and production of acid fermentation products. In some embodiments, the monitoring comprises monitoring one or more of % dry matter (DM) conversion, % of theoretical sugars converted, fermentable sugar concentration, and alcohol concentration.

In some embodiments, the presently disclosed subject matter provides a system for converting biomass to a biofuel, the system comprising:

a treatment facility for processing liquid biomass extract; and a network comprising one or more pipelines for providing liquid biomass extract to the treatment facility from one or more remotely located liquid biomass extract production sites, wherein each of the remotely located liquid biomass extract production sites comprises a biomass source, an atmospherically controlled chamber, an extractor, and a pipeline inlet providing access to the one or more pipelines.

In some embodiments, each of the one or more remotely located liquid biomass extract production sites is at least about 8 kilometers from the treatment facility.

In some embodiments, the presently disclosed subject matter provides a process for converting biomass to biofuel, the process comprising:

providing biomass, wherein providing the biomass comprises harvesting a plant material at a first location, wherein the harvesting is timed to provide plant material comprising a moisture content of between about 70% and about 95%;

placing the biomass into an atmospherically controlled chamber at or in close proximity to the first location for a period of time and under suitable conditions to effect saccharification of the biomass, alcohol fermentation of the biomass, or a combination thereof, thereby providing a liquefied biomass, wherein the liquefied biomass comprises residual solids, biomass-derived water, and water-soluble products, the residual solids comprising non-water soluble polysaccharides and the water soluble products comprising one or more of fermentable sugars and an alcohol;

preparing a slurry comprising residual solids and biomass-derived water;

transporting the slurry to a second location; and treating the slurry at the second location; thereby providing the biofuel.

In some embodiments, preparing the slurry comprises preparing a mixture comprising up to about 40% residual solids. In some embodiments, the process comprises one or more of repeat annual use of the atmospherically controlled chamber and multi-crop use of the atmospherically controlled chamber. In some embodiments, the transporting comprises piping the slurry to the second location.

It is an object of the presently disclosed subject matter to provide systems and processes for preparing liquid biomass extracts and biofuels from plant-derived biomass.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

DETAILED DESCRIPTION

Figure 1:
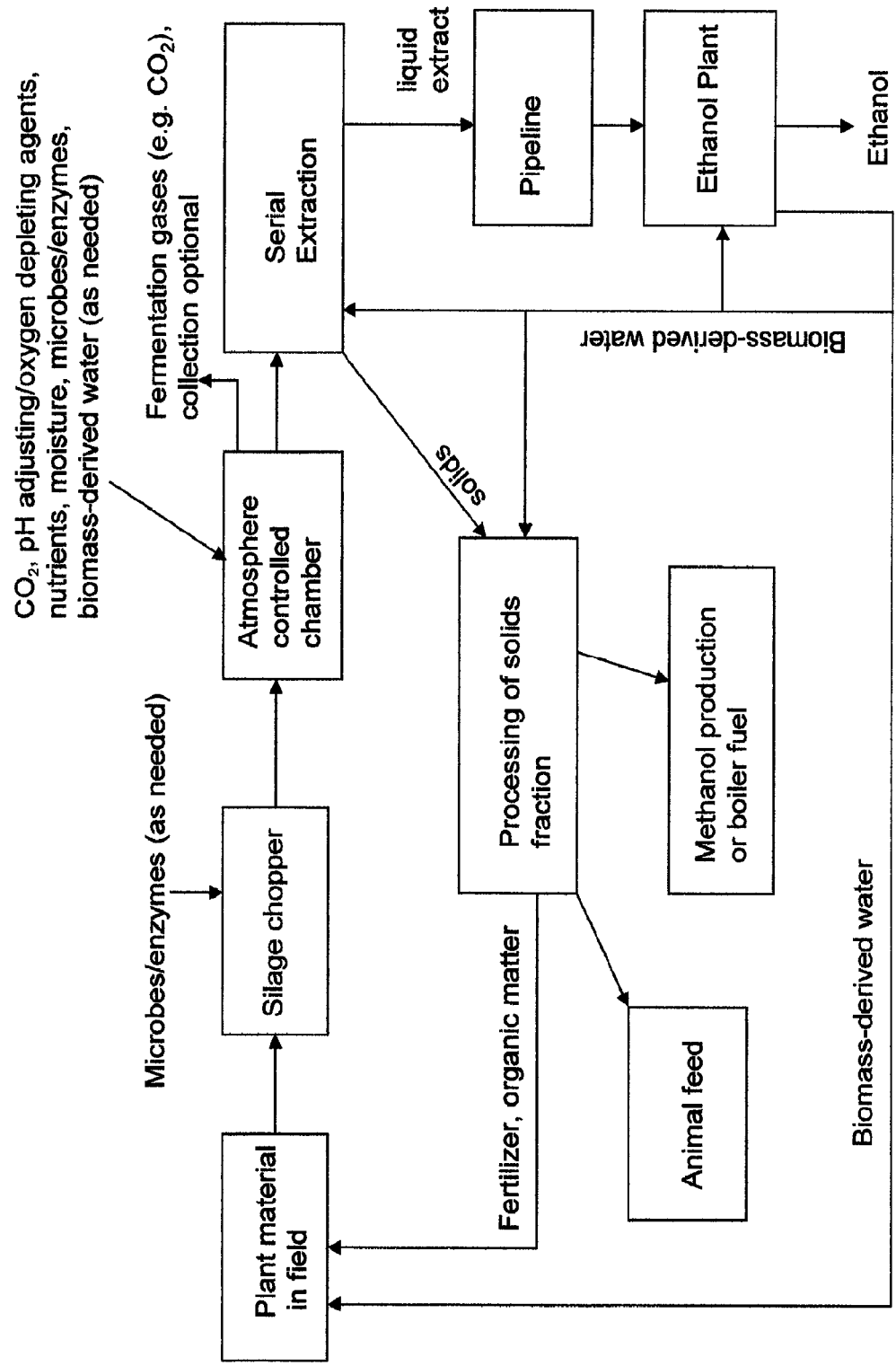
FIG. 1 is a block diagram of a process for converting biomass to ethanol according to an embodiment of the presently disclosed subject matter.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. DEFINITIONS

Following long-standing patent law convention, the terms "a" and "an" mean "one or more" when used in this application, including the claims. Thus, "an enzyme" or "a plant material" can refer to a plurality (i.e., two or more) of enzymes or plant materials.

As used herein, the term "about" modifying any amount can refer to the variation in that amount encountered in real world conditions of producing sugars and ethanol, e.g., in the lab, pilot plant, or production facility. For example, the amounts can vary by about 5%, 1%, or 0.5%. Unless otherwise indicated, all numbers expressing quantities of percentage (%), temperature, time, pH, distance, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

The term "saccharide" refers to a carbohydrate monomer, oligomer or larger polymer. Thus, a saccharide can be a compound that includes one or more cyclized monomer unit based upon an open chain form of a compound having the chemical structure $H(CHOH)_nC(=O)(CHOH)_mH$, wherein the sum of n+m is an integer between 2 and 8. Thus, the monomer units can include trioses, tetroses, pentoses, hexoses, heptoses, nonoses, and mixtures thereof. In some embodiments, each cyclized monomer unit is based on a compound having a chemical structure wherein n+m is 4 or 5. Thus, saccharides can include monosaccharides including, but not limited to, aldohexoses, aldopentoses, ketohexoses, and ketopentoses such as arabinose, lyxose, ribose, xylose, ribulose, xylulose, allose, altrose, galactose, glucose, gulose, idose, mannose, talose, fructose, psicose, sorbose, and tagatose, and to hetero- and homopolymers thereof. Saccharides can also include disaccharides including, but not limited to sucrose, maltose, lactose, trehalose, and cellobiose, as well as hetero- and homopolymers thereof.

The term "oligosaccharide" refers to polysaccharides having a degree of polymerization of between about 2 and about 10.

The terms "fermentable sugar" and "sugar" can be used interchangeably and refer to oligosaccharides, monosaccharides and mixtures thereof that can be used as a carbon source in a fermentation process. Fermentable monosaccharides include arabinose, glyceraldehyde, dihydroxyacetone, erythrose, ribose, ribulose, xylose, glucose, galactose, mannose, fucose, fructose, sedoheptulose, neuraminic acid, or mixtures of these. Fermentable disaccharides include sucrose, lactose, maltose, gentiobiose, or mixtures thereof.

As used herein the term "starch" refers to a polysaccharide polymer of glucose containing $\alpha(1\text{-}4)$ and $\alpha(1\text{-}6)$ glycosidic bonds. In particular, starch refers to a mixture of amylose and amylopectin.

The term "dextrin" refers to a linear, water-soluble oligomer of $\alpha\text{-}(1\text{-}4)\text{-}D\text{-}glucose$. Dextrins can be prepared from the hydrolysis of starch.

The term "cellulose" refers to a polysaccharide of $\beta$-glucose comprising $\beta\text{-}(1\text{-}4)$ glycosidic bonds. The term "cellulosic" refers to a composition comprising cellulose.

The terms "glycosidic bond" and "glycosidic linkage" refer to a linkage between the hemiacetal group of a saccharide and the hydroxyl group of an alcohol (which can be another saccharide).

The term "lignocellulosic" refers to a composition comprising both lignin and cellulose. In some embodiments, lignocellulosic material can comprise hemicellulose, a polysaccharide which can comprise saccharide monomers other than glucose. In some embodiments, the lignocellulosic material can also comprise starch.

"Lignin" is a polyphenolic material. Lignins can be highly branched and can also be crosslinked. Lignins can have significant structural variation that depends, at least in part, on the plant source involved.

Lignocellulosic materials include a variety of plants and plant materials, such as, but not limited to, papermaking sludge; wood, and wood-related materials, e.g., saw dust, or particle board, leaves, or trees, such as poplar trees; grasses, such as switchgrass; whole plant corn; sorghums; sudangrass; grass clippings; rice hulls; bagasse (e.g., sugar cane bagasse); jute; hemp; flax; bamboo; sisal; abaca; hays; straws; corn cobs; corn and sorghum stover; and coconut hair.

The term "biofuel" refers to a fuel that is derived from biomass, i.e., a living or recently living biological organism, such as a plant or an animal waste. Biofuels include, but are not limited to, biodisel, biohydrogen, biogas, biomass-derived dimethylfuran (DMF), and the like. In particular, the term "biofuel" can be used to refer to biomass-derived alcohols (e.g., bioalcohol), such as ethanol, methanol, propanol, or butanol, which can be denatured, if desired prior to use. The term "biofuel" can also be used to refer to fuel mixtures comprising biomass-derived fuels, such as alcohol/gasoline mixtures (i.e., gasohols). Gasohols can comprise any desired percentage of biomass-derived alcohol (i.e., about 10%, 15%, 20%, 25%, 30%, 35%, 40%, 45%, 50%, 55%, 60%, 65%, 70%, 75%, 80%, 85%, 90%, or 95% biomass-derived alcohol). For example, one useful biofuel-based mixture is E85, which comprises 85% ethanol and 15% gasoline.

The term "biocatalyst" refers to both enzymatic catalysts and microbes (e.g., bacteria, fungi, etc.) that produce enzymatic catalysts or otherwise act as catalysts. Biocatalysts can catalyze (e.g., increase the rate of or otherwise facilitate) conversion of one molecule to another. Thus, biocatalysts can catalyze a variety of chemical reactions, such as hydrolysis reactions, isomerization reactions, and the like.

The term "enzyme" refers to a protein that catalyzes the conversion of one molecule into another. The term "enzyme" as used herein includes any enzyme that can catalyze the transformation of a biomass-derived molecule to another biomass-derived molecule. In particular, enzymes include those which can degrade polysaccharides (e.g., cellulose, starch, hemicellulose, or lignocellulose molecules) to provide fermentable sugars and alcohols. Enzymes also include those which can convert one type of sugar into another type of sugar. Enzymes that degrade polysaccharides or that can transform one type of sugar into another can also be referred to herein as "lignocellulose-processing enzymes" or "biomass-processing enzymes".

For use in a process of the presently disclosed subject matter, an enzyme can be specifically selected based on the specific end product desired from the biomass. The enzyme can also be selected to provide a desired property for the biomass contained in an atmospherically controlled chamber or to the liquid obtained from the contained biomass. For example, an enzyme can be selected in order to produce a biomass product of desired viscosity or pH.

As used herein the terms "liquefaction," "liquefy," "liquefact," and variations thereof refer to the process or the products of processes related to increasing the amount of water soluble molecules (e.g., water soluble carbohydrates) in plant-derived biomass. In some embodiments, the term "liquefy" can apply to fermenting (e.g. fermenting to provide an alcohol), saccharifying, or combinations thereof.

As used herein, the terms "hydrolyze," "saccharification," "saccharifying," and variations thereof refer to the process of converting polysaccharides (e.g., cellulose or starch) to fermentable sugars, e.g., through the hydrolysis of glycosidic bonds. Saccharification can be effected with enzymes. The enzymes can be produced in the plant or added to biomass directly (e.g., as a solid or liquid enzyme additive) or can be produced in situ by microbes (e.g., yeasts, fungi, bacteria, etc.). Saccharification products include, for example, fermentable sugars, such as glucose and other small (low molecular weight) oligosaccharides such as monosaccharides, disaccharides, and trisaccharides. Saccharification products can also simply include lower molecular weight polysaccharides than those in the original cellulose or lignocellulose. "Suitable conditions" for saccharification refer to various conditions including pH, temperature, moisture, nutrients, biomass composition, and inoculant composition.

"Fermentation" or "fermenting" can refer to the process of transforming an organic molecule into another molecule using a micro-organism. For example, "fermentation" can refer to transforming sugars or other molecules from biomass to produce alcohols (e.g., ethanol, methanol, butanol); organic acids (e.g., citric acid, acetic acid, itaconic acid, lactic acid, gluconic acid); ketones (e.g., acetone), amino acids (e.g., glutamic acid); gases (e.g., $H_2$ and $CO_2$), antibiotics (e.g., penicillin and tetracycline); enzymes; vitamins (e.g., riboflavin, $B_{12}$, beta-carotene); and/or hormones. Thus, fermentation includes alcohol fermentation. Fermentation also includes anaerobic fermentations.

Fermenting can be accomplished by any organism suitable for use in a desired fermentation step, including, but not limited to, bacteria, fungi, archaea, and protists. Suitable fermenting organisms include those that can convert mono-, di-, and trisaccharides, especially glucose and maltose, or any other biomass-derived molecule, directly or indirectly to the desired fermentation product (e.g., ethanol, butanol, etc.). Suitable fermenting organisms also include those which can convert non-sugar molecules to desired fermentation products.

In some embodiments, the fermenting is effected by a fungal organism (e.g., yeast or filamentous fungi). The yeast can include strains from a *Pichia* or *Saccharomyces* species. In some embodiments, the yeast can be *Saccharomyces cerevisiae*. In some embodiments, the fermenting is effected by bacteria. For example, the bacteria can be *Clostridium acetobutylicum* (e.g., when butanol is the desired fermentation product) or *Corynebacterium glutamicum* (e.g., when monosodium glutamate (MSG) is the desired fermentation product). In some embodiments, the micro-organism (e.g. yeast or bacteria) can be a genetically modified micro-organism. In some instances, the organism can be yeast or other organism having or modified to be active in the presence of high concentrations of alcohol.

The term "alcohol fermentation" refers to the conversion of a fermentable sugar to an alcohol (e.g., methanol, ethanol, propanol, butanol, etc.). The particular product of a given alcohol fermentation can be determined by the biocatalyst used in the fermentation and/or the substrate of fermentation (i.e., the type of fermentable sugar being converted).

In certain embodiments, fermenting can comprise contacting a mixture including biomass-derived sugars with an alcohol-producing biocatalyst, such as yeast or another alcohol-producing microbe. In some embodiments, fermenting involves simultaneous saccharification and fermentation (SSF). The amount of fermentation biocatalyst employed can be selected to effectively produce a desired amount of ethanol in a suitable time and/or upon the sugar content of a given fermentation mixture. The use of alcohol-producing biocatalyst can increase the rate of saccharification by reducing the concentration of sugars, which can inhibit saccharification biocatalysts.

"Suitable conditions" for alcohol fermentation can refer to conditions that support the production of ethanol or another alcohol by a biocatalyst. Such conditions can include pH, nutrients, temperature, moisture, atmosphere, and other factors.

The term "inoculant" refers to any chemical compound, biomolecule (e.g., enzyme) or organism, or mixtures thereof, which are added to freshly cut biomass or to biomass that is going into the atmospherically controlled chamber. Thus, an inoculant can include biomass-processing biocatalysts, including lignocellulose-processing enzymes and microbes (e.g., saccharifying enzymes saccharifying microbes, alcohol-producing enzymes, alcohol-producing microbes, etc.), sterilizing agents (e.g., anti-microbial or bactericidal agents), pH-adjusting agents, electrolytes, oxygen-depleting agents, nitrogen-containing agents, enzyme nutrients and cofactors, softening agents, plasticizers, fillers, and combinations thereof.

The term "pH-adjusting chemical" or "pH-adjusting agent" can refer to any chemical or agent added to control pH in the atmospherically controlled chamber containing biomass, extracted liquids, or solids. Thus, pH-adjusting chemicals and agents can include pH-lowering agents, including mineral acids, organic acids, and acid salts; pH-raising agents, such as bases (e.g., ammonia, and ammonium salts); and buffering agents. Suitable pH-adjusting acids include, but are not limited to, hydrochloric acid, sulfuric acid, citric acid, formic acid, propioinic acid, acetic acid, butyric acid, phosphoric acid, and the like. Suitable pH-adjusting agents also include acid salts, such as sodium diacetate. Suitable bases include, but are not limited to, sodium hydroxide, $Na_2CO_3$, and ammonium hydroxide. Buffering agents include, but are not limited to, $CaCO_3$, $NaHCO_3$, $NH_4Cl$, $NaH_2PO_4$, $K_2HPO_4$, and $KH_2PO_4$. In some embodiments, the buffering agents can act as weak acids or bases, or simply to help maintain the pH within a desired range.

The term "oxygen-depleting agent" refers to additives that can be used in the atmospherically controlled chamber to hasten or maintain the achievement of an anaerobic environment in the chamber. Suitable oxygen-depleting agents include, but are not limited to, chloropicrin. Oxygen-depleting agents also include gases that can be used to displace oxygen, including $CO_2$ gas.

The terms "plasticizer" and "softening agent" refer to materials that cause a reduction in cohesive intermolecular forces along or between polymer chains. Such material can act, for example, to decrease crystallinity, or disrupt bonds between lignin and non-lignin carbohydrate fibers (e.g., cellulose or hemicellulose). Plasticizers and softening agents include, but are not limited to polyols (e.g., glycerol, ethylene glycol), esters of polyols (e.g., glycerol monoacetate), glycol ethers (e.g., diethylene glycol), acetamide, and ethanolamines.

The term "atmospherically controlled chamber" refers to a container inside which atmospheric conditions can be controlled and/or monitored. In some embodiments, the atmospherically controlled chamber is an airtight or air-limiting container. In some embodiments, the atmospherically controlled container is a glass-lined silo, such as commercially available silo originally designed for the ensiling of plant materials to provide animal fodder.

The phrase "at or in close proximity to" can be used to refer to actions or steps in a process that occur or are performed at about the same location or that would not involve transport or travel of appreciable distances. Thus, "at or close proximity to" can refer to actions or steps that occur or are performed within less than about a 8 kilometers radius (e.g., within less than about a 8, 6, 4, 3, 2, or 1 kilometer radius) of one another. In some embodiments, the steps that are performed at or in close proximity to one another are performed in less than about one kilometer of one another. Generally, actions taking place at or in close proximity to one another can occur on the same property, (e.g., on the same farm).

As used herein the terms "remote" and "remotely located" refer to a site or location from which trucking raw high density biomass is economically undesirable or otherwise inconvenient. Thus, a remotely located site refers to a site from which it is advantageous to transport high density biomass products via pipeline. In some embodiments, the remotely located site or location is at least about 8 kilometers from a delivery destination. In some embodiments, the remotely located site is at least about 16, 32, 48, 64, 80, 160, 400, or 800 kilometers from a delivery destination.

The term "transporting" can refer to moving a composition, such as a liquid biomass extract or slurry, from one location to another (e.g., from a first location to a second location). Transporting can involve piping the composition via a pipeline or shipping the composition via ship, barge, tanker, truck, train, or airplane. In some embodiments, transporting comprises piping.

II. CONVERSION OF BIOMASS TO HIGH BULK DENSITY PRODUCTS

Historically, the ensiling of surplus forage has proven a useful and convenient method to preserve feedstuffs for animals, particularly ruminant farm animals, such as cattle. Ensiling is a forage storage and preservation system. Ensiling usually involves primarily acid fermentation, wherein lactic acid bacteria present on the forage or added as an inoculant ferments water soluble carbohydrates to organic acids (e.g., lactic acid) under aerobic and, later, anaerobic conditions. The desired production of lactic acid causes a decrease in pH, which then inhibits any microbes present so that nutrients in the forage are preserved.

More recently, the use of ensiling, either with or without the addition of lignocellulosic enzymes has also been proposed as a cost-effective pretreatment preservation and storage system. Previously dried cellulosic biomass in biomass-to-ethanol conversion processes is re-wetted (usually to about 60% moisture) with non-plant derived water, wherein the ensiled biomass is further heated, saccharified, and fermented following the ensiling, in additional steps. See Chen, Y., et al., *Appl. Biochem. Biotechnol.*, 143, 80-92 (2007); Ren, H., et al. *Appl. Biochem. Biotechnol.*, 336-340, 221-238 (2007); and Murphy, P. T., et al., *Bioresource Technology*, 98, 3106-3111 (2007).

The presently disclosed subject matter relates to processes and systems for converting low bulk density biomass to a high bulk density biomass-derived product, such as high sugar content plant syrup or a high water content ethanol solution. In some embodiments, the presently disclosed processes can be used to increase bulk density of biomass-derived materials from as low as 35.3 kilograms/cubic meter to about 961 kilograms/cubic meter.

In particular, the presently disclosed process relates to a thermogenetic, enzymatic, chemical, and/or microbial conversion process to condense fresh biomass and, in some embodiments, to transport the extracted water soluble carbohydrates, fermentable sugars and/or biofuel-containing solutions to a fermentation or distillation facility. Thus, the presently disclosed subject matter generally relates to processes involving the solid-state saccharification and/or alcohol fermentation of biomass materials wherein the solid-state treatment comprises the primary or only saccharification step in the conversion of the raw biomass materials. The conditions can be controlled so that alcohol is the primary fermentation product or so that the sugars are extracted from the biomass being treated prior to significant (i.e., greater than 10%, 20%, 30%, 40% or 50%) conversion of the sugars to an acid fermentation product. In some embodiments, the treatment conditions are controlled to maximize alcoholic fermentation and/or such that the treatment comprises simultaneous saccharification and alcohol fermentation of the biomass.

Liquid from the treated biomass is subsequently extracted to provide a liquid biomass extract comprising biomass-derived water and water-soluble biomass-derived molecules such as fermentable sugars and alcohols. The liquid biomass extract can also include water soluble polysaccharides that can be further saccharified and then fermented.

Treatment of the raw biomass materials can be accomplished using conventional harvesting and silo-related equipment, close to the site of biomass production. For example, plant materials can be converted to the high bulk density liquid extract product on the farm on which the plant material is grown and harvested.

In some embodiments, the presently disclosed subject matter provides a process for converting biomass to a liquid biomass extract comprising fermentable sugars; the process comprising:

providing biomass, wherein providing the biomass comprises harvesting plant material, wherein the harvesting is timed to provide plant material comprising a moisture content of between about 70% and about 95%;

placing the biomass into an atmospherically controlled chamber for a period of time and under suitable conditions to effect saccharification of the biomass, alcohol fermentation of the biomass, or combinations thereof, thereby providing a liquefied biomass, wherein the liquefied biomass comprises residual solids, biomass-derived water, and water-soluble products, the water soluble products comprising fermentable sugars or fermentable sugars and an alcohol; and serially extracting the liquefied biomass, wherein serially extracting the liquefied biomass comprises:

removing a first portion of the liquefied biomass from the chamber prior to significant degradation of the fermentable sugars to acid fermentation products;

collecting at least a portion of the biomass-derived water and water soluble products from the first portion of the liquefied biomass; and repeating the removing and collecting for one or more additional portions of the liquefied biomass;

thereby providing a liquid biomass extract and a residual solids fraction.

The heat needed to affect saccharification and/or alcohol fermentation of the biomass (i.e., to provide the liquefied biomass) can be provided by the process itself through fresh plant cell respiration, enzymatic, and microbial activity. For example, the piling of the biomass in the chamber can raise the temperature of the biomass above the ambient temperature. Among other things, the density and moisture content of the piled biomass can affect the amount of temperature increase that can be achieved. In particular, the plant-derived heat can provide suitable conditions for the activity of endogenous and/or exogenous plant-degrading enzymes or microbes. By taking advantage of the heat produced by the enclosed pile of plant matter and/or the enzymatic and microbial activity, the energy requirements typically needed for biomass saccharification can be considerably reduced. In particular, in some embodiments, provision of the liquefied biomass (e.g., saccharification and, in some embodiments, partial alcohol fermentation) is accomplished in the absence of additional heat (i.e., in the absence of any externally provided heat, such as heat not produced by plant cell respiration, microbial/enzymatic activity, or the ambient temperature).

The biomass density, and thus, the temperature within the atmospherically controlled chamber can be controlled by chopping the biomass. Commercially available silage choppers can be used to chop the biomass after harvesting. For example, the biomass can be chopped to a theoretical length of cut (TLC) of between about 0.3 and about 1.3 centimeters. The biomass can also be ground.

The size of the atmospherically controlled chamber, particularly the height of the chamber, can also affect the biomass density. In some embodiments, the atmospherically controlled chamber is an upright silo. Suitable silos include commercially available enameled steel silos, also known as glass-lined silos.

Generally, the biomass should not be allowed to dry prior to introduced into the chamber (i.e., the plant material is "freshly harvested"). Thus, the biomass should be chopped and loaded into the atmospherically controlled chamber less than 24 hours after being harvested. In some embodiments, the time from field to chamber is even shorter (i.e., less than about 20, 18, 16, 14, 12, 10, 9, 8, 7, 6, 5, 4, 3, 2, or 1 hour). In some embodiments, the time from field to chamber is within about 20 minutes.

In order to aid in the saccharification and/or alcohol fermentation of the biomass, an inoculant comprising one or more biomass-processing biocatalyst can be added to the biomass. The inoculant can be added during chopping, as the biomass is introduced to the atmospherically controlled chamber, or at any point during the chopping or chamber filling process. For example, the inoculant can comprise one or more biomass-processing biocatalyst to effect saccharification and/or alcohol fermentation of the biomass (e.g., a lignocellulose-processing enzyme, an alcohol-producing microbe, etc.). Thus, in some embodiments, the biomass is inoculated with an ethanol-producing or other alcohol-producing microbe. In some embodiments, the biomass is inoculated with both a lignocellulose-processing enzyme (i.e., a cellulose-, hemicellulose-, starch-, or lignin-degrading enzyme) and an ethanol-producing microbe. In some embodiments, the biomass comprises, at least in some portion, transgenic plant material that contains one or more lignocellulose-processing enzyme.

The inoculant can also include one or more additional additives that can control atmospheric, thermal, and/or chemically-related conditions inside the chamber, including, but not limited to a biocatalyst nutrient, a biocatalyst growth factor, a pH-adjusting agent, an electrolyte, a nitrogen-containing chemical, an antimicrobial agent, an oxygen-depleting agent, a beneficial microbe, a plasticizer, a softener, and combinations thereof. The process can further comprise monitoring the contents (e.g., gases, seepage, or solids) of the atmospherically controlled chamber at one or more locations in the chamber to determine one or more of the pH, temperature, oxygen gas content, escaping gases (i.e., gases produced by the biomass, such as by plant cell respiration and/or enzymatic and microbial activity, including, but not limited to $CO_2$ and $NO_2$), microbial activity, enzymatic activity, % dry matter (DM) conversion, % of theoretical sugars converted, fermentable sugars concentration, alcohol concentration, plant material-derived acid concentration (e.g., lactic acid concentration), and microbial nutrient concentration. In particular, the monitoring can be used to determine when to begin extraction of the liquefied biomass.

In some embodiments, water soluble products and at least about 80% of the biomass-derived water is extracted from the liquefied biomass to provide the liquid biomass extract. In some embodiments, at least about 85% of the biomass-derived water is extracted from the liquefied biomass to provide the liquid biomass extract. In some embodiments, at least about 90% or at least about 95% of the biomass-derived water is extracted from the liquefied biomass to provide the liquid biomass extract.

In some embodiments, the liquid biomass extract comprises biomass-derived water and an alcohol. In some embodiments, the liquid biomass extract comprises biomass-derived water and fermentable sugars. In some embodiments, the liquid biomass extract comprises biomass-derived water, fermentable sugars, and an alcohol. Thus, the liquid biomass extract can have a composition that includes biomass-derived molecules that can be used in the production of biofuels without further saccharification.

Depending on the conditions within the chamber and upon the content of the biomass, the liquid biomass extract can also include additional water-soluble molecules related to the biomass treatment process. For example, the liquid biomass extract can include unfermented water-soluble carbohydrates that can require further hydrolysis prior to fermentation, as well as other fermentation products (although generally as minor constituents), including organic acids, such as acetic acid, lactic acid, butyric acid, and propionic acid.

The liquid nature of the biomass extract allows for cost-effective and convenient storage and transport of useful plant-derived molecules. For example, the liquid biomass can be stored at the site of production or elsewhere in any suitable liquid storage container. In some embodiments, the liquid biomass extract can be transported from the treatment and extraction location to a central storage or collection facility, or directly to any suitable site for further processing (e.g., a conventional ethanol plant, either previously existing or newly built) so that the components in the liquid biomass extract can be further fermented or separated from one another. Transportation of the liquid biomass extract can be by any convenient liquid transport method, such as by truck, rail, ship (e.g., tanker, barge, etc.), air, or pipeline. In some embodiments, the alcohol in the liquid biomass extract can be separated from the other components via distillation or another drying technique (e.g., storage over sieves) to provide a purified alcohol. The purified alcohol can be denatured or mixed with other fuels (e.g. gasoline) to provide a biofuel blend, if desired.

When possible, pipeline transport of liquids can be particularly cost effective. While the piping of pure bioethanol can be cost prohibitive due to the hydroscopicity of ethanol, the present processes can involve piping an inpure liquid intermediate of bioethanol production which already contains water. Thus, in some embodiments, the presently disclosed subject matter provides a method for converting biomass to biofuel that comprises converting raw biomass feedstock to a high density liquid product at or near the site of biomass harvesting, and then transporting the high density liquid product via pipeline to a site for further processing and/or purification of the biofuel.

In some embodiments, the presently disclosed subject matter provides a process for converting biomass to biofuel, the process comprising:

providing biomass, wherein providing the biomass comprises harvesting a plant material at a first location wherein the harvesting of the plant material is timed to provide a plant material comprising a moisture content of between about 70% and about 95%;

placing the biomass into an atmospherically controlled chamber at or in close proximity to the first location for a period of time and under suitable conditions to effect saccharification of the biomass, alcohol fermentation of the biomass, or a combination thereof, thereby providing a liquefied biomass, wherein the liquefied biomass comprises residual solids, biomass-derived water, and water-soluble products, the water soluble products comprising one or more of fermentable sugars and an alcohol;

extracting at least a portion of the biomass-derived water and the water-soluble products from the liquefied biomass, thereby providing a liquid biomass extract and a residual solids fraction;

transporting the liquid biomass extract to a second location; and treating the liquid biomass extract; thereby providing the biofuel.

Generally, the first and second locations can be at least about 8 kilometers apart. In some embodiments, the transporting comprises piping. Thus, the transporting can comprise piping the liquid biomass at least about 8, 16, 24, 32, 40, 48, 56, 64, or 72 kilometers. In some embodiments, the first and second locations are at least about 80 kilometers apart. Thus, the transporting can comprise piping the liquid biomass at least about 80, 100, 120, or 140 kilometers. In some embodiments, the first and second locations are at least about 160 kilometers apart. Thus, the transporting can comprise piping the liquid biomass extract at least about 160, 200, 240, 280, 320, 400, 480, 640, 800, or more kilometers.

In some embodiments, the alcohol is ethanol. In some embodiments, the biofuel comprises ethanol (e.g., the biofuel is ethanol or an ethanol blend).

In some embodiments, the liquefied biomass is serially extracted in a portion-wise manner. Extraction or serial extraction can be timed to occur prior to significant conversion of sugars to organic acids.

In some embodiments, components of the liquid biomass extract other than alcohol can be collected and used. For examples, sugars from the liquid biomass extract can be collected and used in the food or pharmaceutical industry. The biomass-derived water (and/or the nutrients it can contain) can also be collected and recycled. For example, the biomass-derived water can be recycled for use in the presently disclosed processes, as a diluent in a post-saccharification fermentation step, as a diluent for saccharification of biomass being processed at a conventional ethanol plant without an solid-phase pretreatment step, as cooling water in a distillation step, as cooling water during any process step, to treat residual biomass-derived solids produced during the process, or to irrigate a biomass crop.

FIG. 1 is a block diagram showing an embodiment of the presently disclosed subject matter wherein plant-derived biomass is converted to ethanol. As illustrated in FIG. 1, green biomass, (i.e., freshly harvested plant material harvested at a moisture content of at least about 70%) can be harvested using conventional harvesting equipment for the purpose of biofuel production or during the course of harvesting corn grain for other uses. In some embodiments, the biomass can comprise corn (e.g., whole plant corn, corn stover, corn cobs, corn grain, and/or mixtures thereof). In some embodiments, the corn-derived biomass can comprise corn stover. The biomass material can be fed into a silage chopper, chopped to a suitable size and then fed into a suitable atmospherically controllable chamber, such as a conventional storage silo. In some embodiments, referring again to FIG. 1, lignocellulose-processing enzymes and/or alcohol-producing microbes or enzymes can be added to the biomass during chopping to facilitate even mixing of the enzymes and/or microbes in the biomass.

Once the biomass is placed within the atmospherically controlled chamber, conditions in the chamber can be adjusted and/or monitored to promote and/or monitor conversion of the lignocellulosic components of the biomass, for example, by the addition of $CO_2$ gas to promote anaerobic conditions, or through the addition of other agents (e.g., pH adjusting agents, oxygen depleting agents, nutrients, or recycled, biomass-derived, extracted water). Gases produced by the biomass (e.g. $CO_2$) can be monitored and recovered for later use. After a period of time, such as when the biomass or liquid seepage from the biomass comprises a given concentration of alcohol or sugars, the biomass (now referred to as "liquefied biomass") can be removed from the chamber and extracted to remove all or at least some portion of the liquid components from the remaining solids. For example, about 80% of the total fluids or of the biomass-derived water can be extracted, thereby providing a liquid biomass extract (e.g., a plant syrup or high water content ethanol product). The remaining material in the extracted liquefied biomass, i.e., the remaining biomass-derived water, water soluble components, and the non-water soluble components, such as remaining unhydrolyzed cellulose, starch, hemicellulose and lignocellulose, lignins, and the like, can be used for a variety of purposes. For example, the residual solid material can be treated for use as a fertilizer or an animal feed, for methanol production, or as boiler fuel.

Referring again to FIG. 1, the liquid biomass extract can be introduced into a pipeline and pumped to a traditional ethanol plant, where fermentation and/or purification can occur. In some embodiments, the purification can involve distillation, thereby providing ethanol and water. The water can be recycled and used in various steps within the process to minimize or eliminate the need for non-plant water sources. As shown in FIG. 1, the water can be used to irrigate the field where the biomass is grown to help provide new biomass, to dilute the raw biomass feedstock for saccharification or fermentation, for processing of the residual solids fraction, and/or during steps (e.g., distillation) occurring at the ethanol plant.

III. BIOMASS CONSIDERATIONS

Any suitable biomass material can be used. "Biomass" can include any organic, non-fossilized material that is, or is derived from biological organisms, either living or dead. As used herein, "biomass" particularly refers to cellulosic or lignocellulosic biomass material derived from plants, and includes material comprising cellulose and optionally further comprising hemicellulose, lignin, starch, oligosaccharides, and/or monosaccharides. Biomass can also comprise additional components, such as proteins and lipids.

Biomass can be derived from a single source or can comprise a mixture derived from more than one source. For example, biomass can comprise a mixture of material from multiple plant species, multiple hybrids or varieties of the same plant species, and multiple parts of a single plant species. Thus, the plant material can be a mixture of corn stover and various grasses, or a mixture of whole corn plant and corn stover.

In the presently disclosed processes, at least a portion of the biomass material is harvested at or in close proximity to the treatment site comprising the atmospherically controlled chamber. In some embodiments, biomass material that has not been recently harvested (e.g., paper waste or municipal solid waste) or that has been transported from a distance greater than about 8 kilometers can be added to the plant material harvested on site, so long as the costs of acquiring and transporting the added biomass material do not negatively effect the overall cost-effectiveness of the process. In some embodiments, at least 50% of the biomass is plant material harvested at or in close proximity to the atmospherically controlled chamber.

Biomass includes, but is not limited to bioenergy crops, agricultural residues, sludge from paper manufacture, yard waste, wood and forestry waste, municipal solid waste and industrial solid waste. Examples of biomass include, but are not limited to, corn grain, corn cobs, corn stover, corn silage, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, fruits, and flowers.

As used herein, the phrase "plant material" refers to all or part of any plant material that comprises lignocellulose, cellulose, fermentable sugars, starches, and/or other molecules that can be broken down into fermentable sugars. The plant material can be derived from a grain, fruit, legume, seed, stalk, wood, vegetable, root, or a part thereof. In some embodiments, the biomass comprises plant material derived from a plant selected from one or more of the group consisting of maize (i.e., corn), soybean, millet, milo, rye, wheat, triticale, oats, barley, rice, sorghum, sudangrass, switchgrass, *Miscanthus*, alfalfa, cotton, sisal, hemp, jute, turf grass, rape, sunflower, willow, eucalyptus, poplar, pine, willow, tobacco, clover, bamboo, flax, pea, radish, turnip, potato, sweet potato, cassava, taro, beet, sugar beet, sugar cane, and canola. In some embodiments, the biomass comprises one or more of the group consisting of whole plant corn, corn stover, corn cobs, and soybean forage.

The moisture content of the biomass plant material can be adjusted to optimize biomass conversion conditions. In some embodiments, the moisture content of the biomass can be between about 50% and about 90%. The moisture content of plant material used for animal fodder silage is generally lower than about 70% to maintain feeding value, palatability, or to limit seepage that can lead to a loss of nutrients. In the present processes, however, higher moisture content can be beneficial, for example, by facilitating extraction of alcohols and water-soluble carbohydrates (WSC) (which can include both fermentable sugars and non-fermentable polysaccharides) during the extraction process, or by facilitating the reaction of lignocellulose-processing enzymes with lignocellulose in the biomass. In some embodiments, the moisture content of the plant material is at least about 70%. In some embodiments, the moisture content of the plant material is about 75%.

In some embodiments, the harvesting of the plant material used to provide biomass can be timed such that the moisture content is at a desired level. For example, the plant material can be harvested while still green. Thus, in some embodiments, the harvesting of the plant material can be timed to provide a plant material comprising a moisture content of at least 70% (e.g., between about 70% and about 95%). In some embodiments, the harvesting is timed to provide plant material comprising a moisture content of at least about 75% (e.g., between about 75% and about 95%). The plant material can then be placed in an atmospherically controlled container in the absence of a drying period or within a period of time such the moisture content does not decrease by more than 5%.

In addition to moisture, the type of biomass or of the various plant components in a biomass mixture (either plant species, particular plant variety or hybrid, or plant part) can be selected based one or more additional characteristics, including sugar content, cellulose content, lignin content, cost, length of growing season, drought resistance, disease resistance, individual plant size, and tonnage (i.e., tons of plant material produced/hectare). Thus, in some embodiments, a plant material having relatively high sugar or cellulose content can be placed into an atmospherically controlled chamber, or added to plant material having lower sugar or cellulose content and placed into an atmospherically controlled chamber, to optimize biomass conversion conditions (e.g., to increase the overall yield of fermentable sugars or alcohol in the liquid biomass extract, or to increase the overall biofuel yield). Plant materials with low lignin content can be used to facilitate fuller saccharification.

Based on the chemical or general biomass content of various segmented corn hybrids, it appears that corn plants with large amounts of stalk can be advantageous. As described hereinbelow in Example 2, segmented corn plant samples comprising stalk and tassel material comprise a higher percentage of fermentable dry matter than do samples comprising plant leaves, silk and husks. Further, as described hereinbelow in Example 1, most of the biomass content of the stalk is in the portion of the stalk below the ear. Thus, high ear placement can be a factor in optimizing corn plant biomass. Accordingly, in some embodiments, a thick-stalked, high ear-placed corn can be used as a high tonnage biomass feedstock.

Sterility is also expected to increase sugars in corn hybrids. Male sterile corn plants, such as tropical corn hybrids, without kernels, allow for sugars to accumulate in the stalks, and tend to stay greener longer. For example, recent reports describe a tall tropical maize hybrid comprises 25% or more sugar. *University of Illinois at Urbana-Champaign* "If Corn Is Biofuels King, Tropical Maize May Be Emperor," *ScienceDaily*, Oct. 19, 2007. Thus, in some embodiments, the plant material is derived from a male sterile, tropical corn plant generally taller than 3 meters.

In some embodiments, specific corn hybrids, forage-type soybean varieties or hybrids, or varieties of other plants can be developed for use in the presently disclosed processes, wherein said hybrids and varieties maximize metric tons/hectare or convertible sugars/hectare. In some embodiments, a uniform biomass mixture can be developed to optimize the conversion of biomass to sugar and/or alcohol, thereby providing maximal use of biomass-producing acreage.

In some embodiments, harvesting the biomass can comprise harvesting the total "aerial biomass," i.e., all the biomass material of a plant growing above the soil surface. In some embodiments, the height of cut of the plant can be varied to affect the saccharification and/or alcohol fermentation of the plant material. In particular, cut height can be varied because of changes in the lignocellulose content of plant material closer to the soil surface. Many plants have higher lignin and store nitrates in the first few centimeters above the soil surface. For example, a normal silage cut having a cut height of about 15 centimeters can be used to harvest the biomass. The cut height can also be greater than about 15 centimeters or can be lower than 15 centimeters, depending upon the biomass lignin content, field erosion standards, or other parameters.

Seasonal considerations can be taken into account when choosing a biomass source. Biomass plant material can be varied based on seasonal availability. For example, spring cool season plants (e.g., field peas, oats, wheat, barley, etc.) produce the most biomass in the spring, whereas warm season plants (e.g., corn, sorghum, millet, soybeans, etc.) produce the most during the summer. Some cool season plants (e.g., beets, turnips, etc.) accumulate the most biomass in the fall. Biomass harvest can be determined by processing needs and optimum biomass accumulation. With rapid turnover, multiple-cut biomass harvests can occur throughout the growing season. Fast regrowing crops include, but are not limited to forage sorghum, sudangrass, pearl millet, and alfalfa. These crops and other cool season crops (e.g., field pea, forage radish, turnips, beets, rye winter wheat, and winter canola) can be rotated through the presently disclosed systems, thereby maximizing tons harvested and providing crop rotation.

In some embodiments, the biomass comprises plant material from a transgenic plant. In some embodiments, the transgenic plant is engineered to produce one or more protein that facilitates the processing of the biomass to biofuel. In some embodiments, the transgenic plant is a plant that has been engineered to produce one or more lignocellulose-processing enzyme. Types of lignocellulose-processing enzymes are discussed more fully hereinbelow and include, but are not limited to, cellulases, hemicellulases, ligninases, and starch-degrading enzymes, such as amylases. For example, the genome of the transgenic plant can be augmented with a recombinant polynucleotide encoding at least one lignocellulose-processing enzyme (e.g., an amylase) operably linked to a promoter sequence, wherein the polynucleotide sequence is optimized for expression in the plant. The lignocellulose-processing enzyme can be expressed constitutively or tissue-specifically (for example in leaves and stems). In some embodiments, the transgenic plant is engineered to produce an enzyme (i.e., an isomerase) for converting one sugar into another, more easily fermentable sugar. In some embodiments, the transgenic plant is engineered to produce less lignin or more cellulose relative to the wild-type plant. In some embodiments, the transgenic plant can be a plant engineered to produce an antibiotic protein that can retard the growth of undesirable microbes contaminating biomass plant sources.

In some embodiments, the biomass can comprise plant material from a plurality of transgenic plants, wherein each of the plurality of transgenic plants produces a different lignocellulose-processing enzyme or antibiotic protein. In some embodiments, the biomass comprises plant material from a single transgenic plant that produces several different lignocellulose-processing enzymes. In some embodiments, the biomass comprises a mixture of transgenic plant material and non-transgenic plant material. Thus, the transgenic plant material can be used as an enzyme source for the processing of both the transgenic plant material and wild-type plant material, thereby reducing or eliminating the need to add enzyme or microbe inoculant from another source.

Delivery or introduction of a nucleic acid construct into a plant cell to provide a transgenic plant can be accomplished using a variety of methods known in the art. Suitable methods include non-biological methods, such as microinjection, microprojectile bombardment, electroporation, induced uptake, and aerosol beam injection, as well as biological methods, such as direct DNA uptake, liposomes, and *Agrobacterium*-mediated transformation. U.S. Patent Application Publication Nos. 2007/0250961 and 2002/0138878, and PCT International Publication WO 98/16651, each of which is incorporated by reference herein in its entirety, describe methods for transforming plants, as well as a variety of suitable genes related to lignocellulose-processing enzymes.

The processing of harvested plant biomass that occurs prior to introduction into the atmospherically controlled chamber can also be manipulated to affect the outcome of saccharification and/or fermentation processes. Plant materials can be reduced in size to increase packing of the materials, providing for a quicker conversion to anaerobic conditions, or to increase the surface area of the plant material for enzymatic action. Thus, in some embodiments, the biomass can be ground or cut prior to being placed into the chamber, using, for example, a conventional silage chopper. The theoretical length of cut (TLC) of the chopped or ground biomass can be varied to optimize microbial or enzymatic conditions within the chamber. In some embodiments, the TLC of the chopped biomass can be between about 0.3 centimeters and about 1.3 centimeters. Additionally, freezing and thawing the biomass material just prior to being placed into the chamber can aid in breaking down the lignocellulose therein and/or to arrest endogenous microbes. The biomass material could be frozen, for example, using liquid or solid $CO_2$ prepared from $CO_2$ gas collected as a co-product of biomass conversion process. Biomass harvesting can also be timed to follow a freeze.

IV. INOCULANTS AND CONDITIONS

IV.A. Biomass-Processing Biocatalysts

In some embodiments, one or more biomass-processing biocatalyst is added to the biomass as part of an inoculant, for facilitating the saccharification and/or alcohol fermentation of the biomass. The term "biomass-processing biocatalyst" refers to enzymes and microbes (e.g., bacteria, fungi, archaea, or protists) that degrade or convert biomass-derived molecules. For example, the biomass-processing biocatalyst can be a lignocellulose-processing enzyme or an alcohol-producing microbe.

The terms "lignocellulytic enzyme" and "lignocellulose-processing enzyme" refer to enzymes that are involved in the disruption and or degradation of lignocellulose. The disruption of lignocellulose by lignocellulytic enzymes leads to the formation of substances including monosaccharides, disaccharides, polysaccharides and phenols. Lignocellulytic enzymes include, but are not limited to, cellulases, hemicellulases, amylases, and ligninases. Thus, lignocellulytic enzymes include saccharification enzymes, i.e., enzymes which hydrolyze polysaccharides. Saccharification enzymes and their use in biomass treatments have been previously reviewed. See Lynd, L. R., et al., *Microbiol. Mol. Rev.*, 66, 506-577 (2002).

Cellulases are enzymes involved in cellulose degradation. Cellulase enzymes are classified on the basis of their mode of action. There are two basic kinds of cellulases: the endocellulases, which cleave polysaccharide polymer chains internally; and the exocellulases, which cleave from the reducing and non-reducing ends of molecules generated by the action of endocellulases. Cellulases include cellobiohydrolases, endoglucanases, and β-D-glucosidases. Endoglucanases randomly attack the amorphous regions of cellulose substrates, yielding mainly higher oligomers. Cellulobiohydrolases are exocellulases which hydrolyze crystalline cellulose and release cellobiose (glucose dimer). Both types of enzymes hydrolyze-1,4-glycosidic bonds. β-D-glucosidases or cellulobiase converts oligosaccharides and cellubiose to glucose.

Thus, in some embodiments, the biocatalyst is cellulase (E.C. 3.2.1.4), also known as an endoglucanase, which catalyzes the hydrolysis of 1,4-β-D-glycosidic linkages. The cellulase can be of microbial origin, such as derivable from a strain of a filamentous fungus (e.g., *Aspergillus, Trichoderma, Humicola, Fusarium*). Commercially available cellulase preparations which can be used include, but are not limited to, CELLUCLAST™, CELLUZYME™, CEREFLO™, and ULTRAFLO™ (available from Novozymes A/S, Bagsvaerd, Denmark), SPEZYME™ CE and SPEZYME™ CP (available from Genencor International, Inc., Palo Alto, Calif., United States of America) and ROHAMENT® CL (available from AB Enzymes GmbH, Darmstadt, Germany).

Hemicellulases are enzymes that are involved in hemicellulose degradation. Hemicellulases include xylanases, arabinofuranosidases, acetyl xylan esterases, glucuronidases, mannanases, galactanases, and arabinases. Similar to cellulase enzymes, hemicellulases are classified on the basis of their mode of action: the endo-acting hemicellulases attack internal bonds within the polysaccharide chain; the exo-acting hemicellulases act progressively from either the reducing or non-reducing end of polysaccharide chains. More particularly, endo-acting hemicellulases include, but are not limited to, endoarabinanase, endoarabinogalactanase, endoglucanase, endomannanase, endoxylanase, and feraxan endoxylanase. Examples of exo-acting hemicellulases include, but are not limited to, α-L-arabinosidase, β-L-arabinosidase, α-1,2-L-fucosidase, α-D-galactosidase, β-D-galactosidase, β-D-glucosidase, β-D-glucuronidase, β-D-mannosidase, β-D-xylosidase, exo-glucosidase, exo-cellobiohydrolase, exo-mannobiohydrolase, exo-mannanase, exo-xylanase, xylan α-glucuronidase, and coniferin β-glucosidase.

Ligninases are enzymes that are involved in the degradation of lignin. A variety of fungi and bacteria produce ligninases. Lignin-degrading enzymes include, but are not limited to, lignin peroxidases, manganese-dependent peroxidases, hybrid peroxidases (which exhibit combined properties of lignin peroxidases and manganese-dependent peroxidases), and laccases. Hydrogen peroxide, required as a co-substrate by the peroxidases, can be generated by glucose oxidase, aryl alcohol oxidase, and/or lignin peroxidase-activated glyoxal oxidase.

In addition to cellulases, hemicellulases and ligninases, lignocellulolytic enzymes that can be used in the practice of the presently disclosed subject matter also include enzymes that degrade pectic substances. Pectic substances are composed of homogalacturonan (or pectin), rhamnogalacturonan, and xylogalacturonan. Enzymes that degrade homogalacturonan include pectate lyase, pectin lyase, polygalacturonase, pectin acetyl esterase, and pectin methyl esterase. Enzymes that degrade rhamnogalacturonan include α-arabinofuranosidase, β-galactosidase, galactanase, arabinanase, α-arabinofuranosidase, rhamnogalacturonase, rhamnogalacturonan lyase, and rhamnogalacturonan acetyl esterase. Enzymes that degrade xylogalacturonan include xylogalacturonosidase, xylogalacturonase, and rhamnogalacturonan lyase. Other enzymes that may enhance or promote lignocellulose disruption and/or degradation include, but are not limited to, esterases, lipases, phospholipases, phytases, proteases, and peroxidases.

In some embodiments, the lignocellulose-processing enzymes and micro-organisms can be used to hydrolyze starch present in the biomass. Thus, in some embodiments, the inoculant includes at least one amylase enzyme. Examples of suitable amylase enzymes include, but are not limited to α-amylase (which randomly cleaves the α(1-4) glycosidic linkages of amylase to yield dextrin, maltose or glucose molecules) and glucoamylase (which cleaves the α(1-4) and α(1-6) glycosidic linkages of amylase and amylopectin to yield glucose).

The enzyme α-amylase (EC 3.2.1.1) can also be referred to as 1,4-α-D-glucan glucanohydrolase or glycogenase. A variety of α-amylases are known in the art and are commercially available. An α-amylase can be from a fungal or bacterial origin and, in some embodiments, can be expressed by a transgenic plant. The α-amylase can be thermostable.

Glucoamylase (also known as amyloglucosidase) refers to the enzyme that has the systematic name 1,4-α-D-glucan glucohydrolase (E.C. 3.2.1.3). Glucoamylase removes successive glucose units from the non-reducing ends of starch. A variety of glucoamylases are known in the art and are commercially available. For example, certain glucoamylases can hydrolyze both the linear and branched glucosidic linkages of starch, amylose, and amylopectin. Glucoamylase can be from a fungal origin and can be expressed in transgenic plants. The glucoamylase can be thermostable.

Fermentation of fermentable sugars to ethanol can be carried out by one or more appropriate biocatalysts (e.g., enzymes and/or microbes). Suitable ethanol-producing biocatalysts can be micro-organisms selected from bacteria, filamentous fungi, and yeast. The ethanol-producing biocatalyst can be a wild type micro-organism, a mutated micro-organism, or a recombinant micro-organism and can include, for example, *Escherichia, Zymomonas, Saccharomyces, Candida, Pichia, Streptomyces, Bacillus, Lactobacillus*, and *Clostridium*. In some embodiments, the ethanol-producing biocatalyst can be selected from the group consisting of recombinant *Escherichia coli, Zymomonas mobilis, Bacillus stearothermophilus, Saccharomyces cerevisiae, Clostridia thermocellum, Thermoanaerobacterium saccharolyticum*, and *Pichia stipitis*. In some embodiments, the fermentation or other biomass-processing microbe of the presently disclosed processes is an anaerobic microbe.

Biocatalysts for fermentation to produce ethanol include those that have been previously described, or those that can be discovered, produced through mutation, or engineered through recombinant means. In particular, U.S. Patent Application Publication No. 2007/0178569, incorporated herein by reference in its entirety, describes *Clostridium phytofermentans*, an anaerobic bacterium that can ferment cellulosic material to fuel (e.g., ethanol) directly, without another chemical or enzymatic treatment. Other suitable ethanol-producing organisms include those which can utilize carbon monoxide from biomass to produce ethanol, including *Butyribacterium methylotropicum, Clostridium autoethanogenum, Clostridium carboxidivorans*, and *Clostridium ljungdahlii*. See, e.g., U.S. Patent Application Publication No. 2007/0275447, incorporated herein by reference in its entirety, with regard to *Clostridium carboxidivorans*.

Biomass-processing biocatalysts generally have or can be adapted to have a preferred temperature and pH range for activity. In some embodiments, the biocatalysts can (or can be adapted to) operate at pH ranges between 4 and 5. In some embodiments, the biocatalysts can operate at temperatures ranging from ambient temperature to about 45° C. above ambient temperatures. In some embodiments, the optimal pH and/or temperature ranges (the ranges that give maximal activity) of the saccharification and/or fermentation enzymes used as inoculant can be specifically selected so that acid fermentation products (e.g., lactic acid, acetic acid) are minimized. For example, an enzyme can be selected to have an optimal pH range that does not overlap with that of lactic acid fermentation enzymes that can be present in the atmospherically controlled chamber. In some embodiments, the enzymes or microbes can be selected to function under high alcohol and/or sugar concentrations. In some embodiments, the enzymes or microbes can be selected for optimal activity under temperature conditions present in the atmospherically controlled chamber.

The amount of enzyme used can vary depending upon biomass content. In some embodiments, a cellulase/hemicellulase enzyme mixture can be used in an amount of about 10 to about 60 filter paper units (FPU)/g theoretical sugars. In some embodiments, between about 20 and about 40 FPU/g enzyme is used. Enzyme volume can also be adjusted based on temperature, time, moisture, and conversions expected.

IV.B. Other Additives

A number of other inoculant components can be added to the biomass, either in combination with a biomass-processing biocatalyst or alone. While these additives do not directly saccharify or ferment the biomass to alcohols, they can be added to control the rate of saccharification or fermentation, or to control the ratio of products expected in the liquid biomass extract. In some embodiments, a biomass-processing biocatalyst is used in combination with other inoculant additives to provide an optimum environment for the biocatalyst.

In some embodiments, one or more inoculant component is added as a nutrient or growth factor for one or more biomass-processing biocatalyst present in the biomass as harvested or intentionally added. For example, the inoculant can include one or more growth factor or nutrient, such as a vitamin or mineral. Vitamins include, but are not limited to, biotin, folic acid, pyridoxine, riboflavin, urea, yeast extract, thymine, tryptone, adenine, cytosine, guanosine, uracil, nicotinic acid, pantothenic acid, B12 (cyanocobalamin), and p-aminobenzoic acid. Minerals can include, but are not limited to, $MgSO_4$, $MnSO_4$, $FeSO_4$, $CaCl_2$, $CoCl_2$, $ZnCl_2$, $CuSO_4$, $AlK(SO_4)_2$, $H_3BO_3$, $Na_2MoO_4$, $NiCl_2$, $NaWo_4$, and hydrates thereof.

In some embodiments, the inoculant includes one or more chelator or surfactant. In some embodiments, the inoculant includes a softener or plasticizer. The inoculant can also include some solid material as a filler or extender to help mix the inoculant components into a uniform composition and/or to help spread the inoculant in the biomass evenly.

In some embodiments, the inoculant includes a pH-adjusting agent to raise or lower the pH of the liquefying biomass or to help maintain the pH in a desired range. The pH-adjusting agent can be an acid, a base, a buffering agent, or combinations thereof. Thus, in some embodiments, the inoculant can include one or more pH-adjusting agent such that the pH within the chamber can be adjusted or maintained under optimal conditions for the lignocellulytic and/or alcohol fermentation enzymes and microbes present or added to the biomass.

The inoculant can also include an electrolyte, such as NaCl or KCl. The electrolyte can be used to control the water activity of the liquids within the biomass.

In some embodiments, the inoculant can include one or more nitrogen-containing agents, such as, ammonia, ammonium hydroxide, ammonium chloride, urea, ammonium nitrate, or ammonium phosphate. The nitrogen-containing agent can act as a nutrient, a pH-adjusting agent, an oxygen-depleting agent, or to add nutritional value to the residual solids produced during the process.

In some embodiments, the inoculant can contain an antimicrobial agent directed to inhibit the activity of an undesirable microbe present in the chamber. For example, the inoculant can comprise an antibacterial agent to inhibit the activity of a lactic acid bacteria or any other microbe that utilizes fermentable sugars for a purpose other than alcohol production.

In some embodiments, the inoculant can comprise one or more oxygen-depleting agent, used to facilitate the achievement of an anaerobic environment in the chamber. Solid oxygen-depleting agents include, but are not limited to, chloropicrin. In some embodiments, the oxygen-depleting agent is a gas, such as $CO_2$, $N_2$, or $H_2$. The gas can be produced by a microbe or by enzymatic action within the chamber, or the gas can be specifically added to the chamber directly. Thus, in some embodiments, an oxygen-depleting gas such as $CO_2$ is added to the chamber during or immediately after filling with the biomass, displacing some or all of the $O_2$ gas present.

In some embodiments, at least a portion of the inoculating material can be added during biomass chopping to facilitate even mixing of the inoculant. In some embodiments, one or more biomass-processing biocatalyst can be added to the plant material during the chopping. In some embodiments, one or more pH-adjusting agent, nitrogen-containing agent, or nutrient is added to the plant material during chopping. In some embodiments, at least a portion of the inoculant is added while the plant material is being placed into the chamber. Additionally, the atmospherically controlled chamber can be adapted so that inoculant can be added at any time after the plant material has been originally added into the chamber, to adjust the saccharification and/or fermentation rate as necessary. For example, additional biocatalyst or pH-adjusting agents can be added at any time after the plant material has been introduced into the chamber to adjust conditions to promote desired saccharification or fermentation or to reduce undesirable fermentation reactions.

IV.C. Chamber Conditions and Monitoring

When anaerobic biocatalysts are employed, conditions within the chamber can be controlled to achieve anaerobic conditions as rapidly as possible. As noted above, oxygen-depleting agents can be added, before, during, or after the filling of the chamber with the biomass. Other factors, such as length of cut, biomass compaction, and/or initial sugar content can be used to speed achievement of anaerobic conditions, as well.

The providing and placing of the biomass into the chamber is usually performed in the absence of added water (or with the addition of only a minimal amount of water used to provide an inoculant solution that can be sprayed onto the biomass). Thus, in some embodiments, the presently disclosed processes provide saccharification and/or fermentation with biomass-derived water as the sole liquid medium. In some embodiments, the biomass-derived water accounts for at least about 90%, at least about 95%, or at least about 98% of the water present in the chamber.

Under conventional lactic acid fermentation ensiling conditions, the temperature of ensiled biomaterials, such as corn stover, can be about 15-20° C. above ambient temperature (i.e., the temperature of the plant material prior to being ensiled). According to the presently disclosed processes, heat inside the chamber can be controlled by length of chop, moisture content, sugar content, enzyme load, packing system, natural microbe control, the addition of non-plant nitrogen, the size (and/or depth) of the container, inoculation with beneficial microbes, and with heat exchange or cooling systems. For example, increased moisture content and shorter cut length can combine to increase heat in the atmospherically controlled chamber above that typically observed during the ensiling of plant material for use as fodder, when high heat is undesirable because it can cause a loss of nutrient value. In some embodiments higher heat levels can be desired to decrease endogenous microbes and/or to optimize efficiency of inoculations suitable for higher temperatures, such as enzymes developed to be active at higher temperatures (i.e., greater than about 50° C. or about 60° C.).

In some embodiments, conditions within the chamber can be controlled so that temperatures reach between about 25-49° C. above the temperature outside of the chamber. The heat can be used to increase the conversion of biomass to sugars and ethanol, in the absence of heat added from an outside source. By using the heat generated by the conditions in the chamber, the presently disclosed processes can reduce costs generally associated with biomass processing that involves the addition of heat to biomass/saccharification enzyme slurries and fermentation baths.

During the saccharification or saccharification/alcohol fermentation, the biomass can be monitored to determine when to extract the liquefied biomass. Based on monitoring data, it can also be determined that additional inoculant be added to the chamber or that the conditions be altered in some other manner to increase saccharification and/or alcohol production or to decrease acid fermentation.

Thus, in some embodiments, the placing of the biomass into the atmospherically controlled chamber comprises filling the chamber with biomass; and monitoring one or more of temperature, atmospheric oxygen level, escaping gases, pH, production of saccharification products, production of alcohol fermentation products, and production of acid fermentation products.

Monitoring the production of saccharification products can comprise monitoring concentrations of lignocellulose saccharification products in the liquefying biomass or the liquid seepage therefrom, including, but not limited to, WSC, fermentable sugars, and lignin. Monitoring alcohol fermentation can comprise monitoring concentrations of alcohols, such as amounts of ethanol and butanol. The monitoring of acid fermentation products can comprise monitoring for levels of lactic acid, butyric acid, and acetic acid. When possible, residual solid biomass can be assayed for loss of dry matter (DM) as an indication of the conversion of lignocellulose to fermentable sugars and/or alcohol. Further, the amount of sugars theoretically present based on chemical analysis of the original biomass DM can be calculated and compared to the amount of sugars and/or alcohol actually present at a given time during the saccharification or saccharification/alcohol fermentation. When a desired level of biomass conversion is reached, the biomass can be extracted. Concentrations of products can also be monitored as a function of time, to determine the general rate of saccharification or alcohol fermentation in the chamber.

Based on the presence or relative concentrations of acid fermentation products to saccharification products and alcohols, pH-adjusting agents and/or additional biocatalyst inoculants can be added to the biomass mixture. For example, the presence of high levels of lactic, acetic, or butyric acid can indicate that fermentable sugars are being wasted in alternative fermentation processes, and correction of the conditions within the chamber can be performed. The pH can be adjusted to favor alcohol fermentation biocatalysts or additional alcohol biocatalysts can be added to the chamber.

Conversion of the biomass will usually take at least about 20 hours, but could also take several days or months. In some embodiments, the period of time is between about 20 hours to about 21 days. In some embodiments, the period of time is between about 24 hours to about 72 hours. In some embodiments, the period of time is between about 24 hours and about 48 hours or between about 24 hours and about 36 hours. The period of time can vary depending on factors including, but not limited to, the type of biomass used, the amount of biomass used, moisture of incoming biomass, the desired composition of the liquid biomass extract, the amount of biocatalysts present, temperature, and pH.

Individual steps or the entire processes of the presently disclosed subject matter can be repeated as desired reusing the same atmospherically controlled chamber a plurality of times over the course of a single year. Thus, the chamber can be reused in the saccharification and/or alcohol fermentation of several batches of biomass annually. In some embodiments, the chamber can be reused for multi-crop saccharification and/or alcohol fermentation (i.e., the saccharification and/or alcohol fermentation of several different types of crops sequentially).

IV.D. Analytical Methods

By "dry matter" or "dry weight" of biomass is meant the weight of the biomass having all or essentially all water removed. Dry matter (DM) can be measured according to American Society of Testing and Materials (ASTM) Standard E1756-01 (Standard Test Method for Determination of Total Solids in Biomass). DM of paper-related biomass can be determined via Technical Association of the Pulp and Paper Industry, Inc (TAPPI) Standard T-412 om-02 (Moisture in Pulp, Paper, and Paperboard).

The moisture content of plant material can be tested according to a variety of methods known in the art. For example, the moisture content of plant material can be calculated based upon the weight lost during drying of the plant material (e.g., the difference between the weight of the raw biomass and the biomass DM, i.e., 1-DM or 100%-% DM). Moisture content of plant material can also be tested using commercially available moisture meters.

Dry chemistry analysis of DM, ash, neutral detergent fiber (NDF) (e.g., lignin, hemicellulose, and cellulose), acid detergent fiber (ADF), lignin, and crude protein content can be performed, for example, by near infrared reflectance spectroscopy (NIRS). Other established feed analysis procedures can also be used to analyze biomass feedstocks and saccharified biomass to determine levels of neutral detergent fiber (NDF), NDF digestibility, and non-structural carbohydrates (NSC). See, e.g., Chen, Y., et al., *Appl. Biochem. Biotechnol.*, 143, 80-92 (2007).

Soluble sugars (e.g., glucose, cellobiose, xylose, galactose, arabinose, mannose, etc.), acetamide, lactic acid, and acetic acid present in biomass liquid extracts can be measured via HPLC. For more information concerning suitable HPLC methods for the determination of carbohydrates, soluble sugars and other water soluble components, see U.S. Patent Application Publication No. 2007/0031953. Water-soluble carbohydrate can also be determined using the phenol sulfuric acid method, while alcohol content can be determined using gas chromatography. See Pedroso, et al., *Sci. Agric.*, 62(5), 427-432, 2005. Ethanol content can also be analyzed via enzymatic assays using alcohol dehydrogenase, described, for example, in Chen, Y., et al., *Appl. Biochem. Biotechnol.*, 143, 80-92 (2007).

The pH of the biomass within the atmospherically controlled chamber can be determined by shaking a small sample of biomass removed from the chamber with water for a minute or two and analyzing the pH of the water with commercially available pH-sensitive paper. Alternatively, a pH meter can be used for more accurate readings.

V. EXTRACTION

Methods for the extraction of the biomass-derived water and water soluble biomass products from the liquefied biomass include, but are not limited to, decanting, filtering (including vacuum filtering), pressing, centrifuging, and other solid-liquid extraction methods. Thus, in some embodiments, the extracting comprises one or more of centrifuging the liquefied biomass, pressing the liquefied biomass, and decanting the liquefied biomass. In some embodiments, the liquefied biomass is serially extracted, in a portion-wise manner. If serial extraction is employed, portions of liquefied biomass are unloaded from the bottom of the atmospherically controlled chamber and extracted, one at a time, until all of the liquefied biomass is extracted, or until a desired amount of the liquefied biomass is extracted.

While the majority of the liquids present in the biomass are extracted to provide the liquid biomass extract, extraction is not always exhaustive. In some embodiments, the liquids biomass extract comprises about 80% of the biomass-derived water from the biomass. The majority of the water soluble molecules present in the liquefied biomass can be dissolved in the biomass-derived water. Thus, the liquid biomass extract can also comprise fermentable sugars and alcohol. In some embodiments, the liquid biomass extract can be concentrated to increase concentrations of desired molecules. In some embodiments, the liquid biomass extract can comprise up to about 90% alcohol. In some embodiments, the liquid biomass extract can comprise between about 10% and about 90% alcohol.

The residual solids fraction can comprise about 20% of the plant-derived water, as well as the non-water soluble molecules from the liquefied biomass, including lignins and unhydrolyzed cellulose and hemicellulose. The residual solids fraction of the biomass can be washed with water to remove additional adsorbed sugars, if desired, following any previously performed extraction step.

The liquid biomass extract can be stored for a time in a suitable liquid storage facility prior to transportation to a second location for further processing for the production and/or purification of the biofuel. Following extraction, the pH of the liquid biomass extract can be adjusted to better facilitate storage or transport. For example, when the pH of the liquid biomass extract is relatively acidic (e.g., less than about 6 or less than about 5), it can be adjusted to a neutral range (i.e., between about 6 and about 8, or between about 6.7 and about 7.6) so as to be less corrosive to various materials used in the construction of liquid storage containers, tanker trucks or pipelines. In addition, additional enzymes and/or microbes can be added to the liquid biomass extract to affect additional saccharification, alcohol fermentation, and/or to control the viscosity of the extract (e.g., to halt gelling of any remaining polysaccharides).

VI. PROCESS MACHINERY AND ATMOSPHERICALLY CONTROLLED CHAMBERS

The processes and systems of the presently disclosed subject matter can make use of currently available commercial harvesting equipment (e.g., forage harvesters), silage choppers, silos, silo loading and unloading equipment, extraction equipment and pumping equipment. Extraction of the liquefied biomass can also take advantage of screening machinery, centrifuges, decanters, concentrators, and other extracting machinery (e.g., countercurrent extractors, screw-conveyor extractors, or vacuum-belt extractors) presently used in the ethanol production. Suitable equipment can be provided, for example, from Westfalia Separator, Inc. (Northvale, N.J., United States of America), Louisiana Chemical Equipment Co., L.P., (Baton Rouge, La., United States of America), and TM Industrial Supply, Inc. (Erie, Pa., United States of America).

The atmospherically controlled chamber of the presently disclosed processes can include any suitable container that allows for control of the atmospheric conditions within and which is made of a material that will not be affected by the enclosed piled biomass or by any added inoculants. The chamber will generally be air tight. The chamber can be a vertical silo or a horizontal silo (e.g., a bunker silo). Possible chambers also include polybags, fuel storage tanks, and lined lagoons. In some embodiments, the atmospherically controlled chamber is a vertical oxygen-limiting silo. Suitable silos include, for example, bulk material SH-type enameled storage tanks manufactured by Vitkovice-Power Engineering, Ltd. (Ostrava, Czech Republic), or equipment commercially available from Nebraska Harvestore Systems, Inc. (Norfolk, Nebr., United States of America).

The chamber can include loading and unloading equipment (e.g., conveyors, hoppers, etc.), as well as equipment for monitoring conditions (e.g. temperature) or the contents of the chamber. The chamber can also include mixing equipment, fans, cooling equipment, and gas tanks and gas inlets and/or outlets for introducing a gas into the chamber or collecting gas from the chamber. In some embodiments, the chamber can have a sloped floor, to aid in collection of liquid seepage or in biomass extraction.

VII. PIPELINE TRANSPORT

As noted above, the pipeline transport of ethanol is generally considered unfavorable due to the hygroscopic nature of ethanol. Recently, a process has been described that involves the simultaneous pipeline transport and saccharification of corn stover, in a process involving the addition of water and enzymes to raw biomass feedstocks at the inlet of a pipeline network, to prepare a slurry containing at least about 20% solids. See Kumar et al., *Bioresource Technology*, 96, 819-829 (2005).

The presently disclosed subject matter is believed to be the first to describe saccharification and/or fermentation of bulk fresh biomass, in the absence of added water or of significant amounts of added water, followed by pipeline transport of a sugar and/or alcohol solution over significant distances, as part of a biofuel production process. The extraction and saccharification (or saccharification/alcohol fermentation) conditions of the presently disclosed processes can be adjusted to provide a liquid biomass extract having a chemical composition, viscosity and pH suitable for piping in pipelines designed for other purposes, including, but not limited to, those designed for the piping of water. Thus, the pipelines can be made of any suitable material and can be of any suitable diameter.

Based on the piping of water, pipelines having a 15 centimeter diameter can deliver about 2,270 liters per minute, while 30 and 40 centimeter diameter pipelines can deliver about 4500 liters/minute. Water pipeline costs vary based upon factors including, but not limited to, the type of pipe, size (i.e., the diameter of the pipe), depth, pressure relief spacing, and pumping needs. For example, a 2.5-3.8 centimeter pipeline can be laid for approximately $3.28-$5.00/meter (i.e., approximately $3,280-$5,000/kilometer). Water pipelines for rural water projects designed to meet various state and federal guidelines can cost more. To avoid freezing in northern latitudes, pipes can be buried at a depth of about 1.5 meters with pressure relief valves about every 762 meters, costing about $10,000 dollars each.

In the presently disclosed processes, costs related to constructing pipeline networks, however, can be offset by the reduction in wear and tear on the local, county, and state roadways caused when biomass is delivered to biofuel production and processing facilities by truck. Pipeline costs for processes involving the transportation of liquid biomass extract can also be offset by reduced pipeline requirements related to the large water supplies typically needed for biofuel facilities that require water to hydrate raw biomass for saccharification and fermentation. For instance, a supply pipeline for supplying 379 million liters per year (mly) of water to a dry-grind corn ethanol production facility is estimated as needing to supply about 6.5 million liters of water per day (4,542 liters/minute). Truck delivery of the same amount of water would require about 288 tanker trucks each day, each holding approximately 22,700 liters of water.

The piping distance of the liquid biomass extract can vary depending upon the distance to the nearest treatment facility for biofuel fermentation and/or purification. The placement and capacity of these facilities can be designed to balance the costs of constructing and maintaining pipeline networks with the costs associated with building and maintaining the treatment facilities. The relative geographical concentration of biomass-producing acreage can also affect the placement and capacity of the facilities. In some embodiments, the liquid biomass extract is piped for a distance of more than about 8 kilometers. In some embodiments, the piping comprises piping the liquid biomass extract for a distance of at least about 80 kilometers. In some embodiments, the piping comprises piping the liquid biomass extract for a distance of at least about 160 kilometers.

In addition to piping or otherwise transporting liquid biomass extracts, the presently disclosed subject matter also provides processes wherein a slurry prepared from the liquefied biomass is transported (e.g., pumped) to a centralized treatment facility from a remote location. In some embodiments, the presently disclosed subject matter provides a process for preparing a biofuel comprising:

providing biomass, wherein providing the biomass comprises harvesting a plant material at a first location, wherein the harvesting is timed to provide plant material comprising a moisture content of between about 70% and about 95%;

placing the biomass into an atmospherically controlled chamber at or in close proximity to the first location for a period of time and under suitable conditions to effect saccharification of the biomass, alcohol fermentation of the biomass, or a combination thereof, thereby providing a liquefied biomass, wherein the liquefied biomass comprises residual solids, biomass-derived water, and water-soluble products, the residual solids comprising non-water soluble polysaccharides and the water soluble products comprising one or more of fermentable sugars and an alcohol;

preparing a slurry comprising residual solids and biomass-derived water;

transporting the slurry to a second location; and treating the slurry at the second location; thereby providing the biofuel. Thus, the slurry can comprise unhydrolyzed and/or partially hydrolyzed lignocellulose in addition to biomass-derived water, sugars and alcohols. The amount of solids in the slurry can be controlled so that the slurry is pipe-able and the slurry is piped to the second location. In some embodiments, the slurry comprises up to about 40% solids (by volume) from the liquefied biomass.

The slurry can be prepared by grinding the liquefied biomass to reduce the remaining solids in size. Biomass-derived water and/or water provided from another source can be added as needed to provide the desired percentage of liquid. In some embodiments, the liquefied biomass can be extracted to provide a residual solids fraction and some of the residual solids fraction can be added back to the liquid biomass extract to provide a slurry prior to piping or other transport.

The slurry can be transported (e.g., piped) for a distance of at least about 8 kilometers or more. The second location can comprise a traditional ethanol production facility, which can be either a pre-existing ethanol production facility or one newly built to receive slurries from the presently disclosed processes. The slurry can be treated to provide a biofuel, such as ethanol, by sequential saccharification and fermentation or via simultaneous saccharification and fermentation. Following saccharification and fermentation, alcohol can be purified by any suitable method.

VIII. BIOMASS LIQUID EXTRACT TREATMENT FACILITIES

Biomass liquid extract treatment facilities of the presently disclosed subject matter can include conventional ethanol-producing facilities for use in preparing biofuels from corn grain and/or other lignocellulosic biomass. The treatment facilities can also be facilities specifically built and designed to process liquid biomass extract or pre-existing facilities.

At the treatment facility, separation of the constituents of the liquid biomass extract, if desired, can be done using a variety of chemical and physical techniques that rely on the different chemical and physical properties of the molecules present (e.g., sugars, organic acids, and phenols), Such techniques, include, but are not limited to, chromatography (e.g., ion exchange, affinity, hydrophobic, size exclusion), electrophoretic procedures, differential solubility, distillation and/or extraction (solid-phase or liquid-liquid).

In some embodiments, the liquid biomass extract comprises plant-derived water and fermentable sugars. Upon arrival of the liquid biomass extract at the treatment facility, the liquid biomass extract can be fermented to convert the fermentable sugars present into alcohol. The fermentation can be performed using any suitable alcohol-producing biocatalyst. In some embodiments, the biocatalyst is an alcohol-producing microbe, such as, yeast. If necessary, yeast nutrients or other microbe nutrients can be added to the liquid biomass extract. The fermenting mixture can provide its own heat or the heat can be artificially maintained at a suitable temperature, i.e., between about 25-45° C., for a period of time sufficient to effect the desired amount of fermentation. When convenient, heating needs can be supplied by burning co-products of the presently disclosed processes, such as lignin. Following fermentation, the ethanol in the fermented liquid biomass extract can be purified according to any suitable technique.

In some embodiments, the liquid biomass extract comprises at least some amount of ethanol. In some embodiments, the liquid biomass extract can comprise between about 10% and about 90% ethanol. The ethanol can be isolated from the liquid biomass extract or from a further fermented liquid biomass extract using methods such as distillation, azeotropic distillation, liquid-liquid extraction, adsorption, gas stripping, membrane evaporation, pervaporation, and the like.

In some embodiments, the by-products (e.g., methanol, phenols) of the process can be used as ethanol denaturants. In some embodiments, the ethanol can be blended with gasoline as a denaturant. For example, about 5% gasoline can be added to distilled ethanol as a denaturant to prevent unauthorized non-fuel use. Alternatively, higher percentages of gasoline can be added to the ethanol to provide a desired gasoline/ethanol fuel blend, such as E85.

In some embodiments, the plant-derived water from the liquid biomass extract is separated and recycled. The plant-derived water can be used to provide at least a portion of the water needs of the treatment facility. For example, if the facility is also used to process raw biomass feedstocks, the water can be used to dilute the raw biomass feedstock for saccharification or fermentation. The water can be used to further dilute liquid biomass extracts prior to a fermentation or distillation step. The water can be used as a coolant in distillation columns. Alternatively, the water can be piped or trucked away from the facility and used elsewhere. In some embodiments, the plant-derived water can be used to irrigate crops for use as biofuel biomass feedstock. In some embodiments, the same pipeline network used to provide the liquid biomass extract to the treatment facility can be used to return biomass-derived water to the harvesting site.

Average corn silage having a yield of 77.6 metric tons/hectare and a moisture content of 65.3% can produce a water yield of about 51,000 kilograms per hectare or about 53,200 liters per hectare. By increasing the corn moisture level to 75%, allowing a 5% loss before saccharification or saccharification/alcohol fermentation, the amount of available biomass-derived water increases to about 57,000 liters per hectare. Thus, the presently disclosed processes can facilitate the capture and reuse of large amounts of water.

IX. CO-PRODUCTS

In addition to bioalcohols, the presently disclosed processes can also produce several additional economically useful co-products.

The solid residuals fraction of the liquefied biomass can comprise lignin, protein, unhydrolyzed and/or partially hydrolyzed lignocellulose, and a variety of other components, including some of the biomass-derived water and water soluble sugars. The solid residuals fraction can comprise useful nutrients, including, but not limited to, nitrogen, phosphorous, potassium and others, which can be useful in feeds and fertilizers. Thus, in some embodiments, the solid residuals faction can be dried to provide an animal feed or a fertilizer that can be used, for example, on fields where biomass is being produced (e.g., to reintroduce unfermented lignin and other constituents to replenish or build soil organic matter). In some embodiments, the solid residuals can be burned to provide fuel for boilers. In some embodiments, the solid residuals can be used to provide methanol. In some embodiments, the solid residuals can be used in the preparation of slurry which can be further saccharified and fermented.

Various additional components in the liquid biomass extract can also be used. For example, in addition to the plant-derived water, phenolic products of lignin hydrolysis and organic acids from acid fermentation reactions can be purified away from the sugar and alcohols present in the liquid biomass extract. In some embodiments, the remaining fermentable sugars can be collected and used, for example as sweeteners, in the food or pharmaceutical industries.

X. SYSTEMS

In some embodiments, the presently disclosed subject matter provides a system for converting biomass to a biofuel, the system comprising:

a treatment facility for processing liquid biomass extract; and a network comprising one or more pipelines for providing liquid biomass extract to the treatment facility from one or more remotely located liquid biomass extract production sites, wherein each of the remotely located liquid biomass extract production sites comprises a biomass source, an atmospherically controlled chamber, an extractor, and a pipeline inlet providing access to the one or more pipelines. In some embodiments, each of the one or more remotely located liquid biomass extract production sites is at least about 8 kilometers from the treatment facility.

Figure 2:
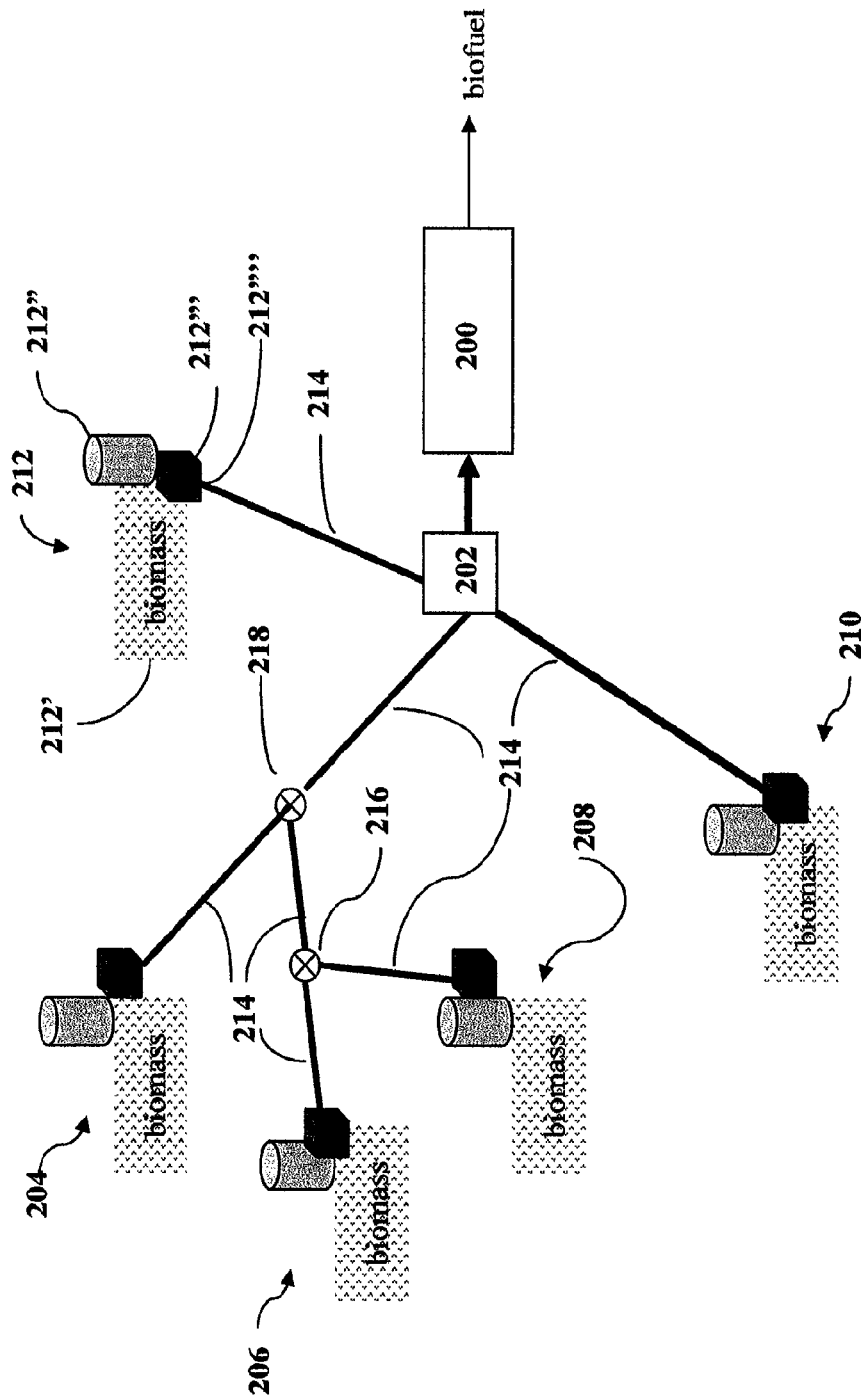
FIG. 2 is an illustration of a system for producing biofuel including a network of pipelines for transporting liquid biomass extract from a plurality of individual biomass extract production sites to a central processing facility.

One example of a system of the presently disclosed subject matter is illustrated in FIG. 2. Treatment facility 200 (e.g., a conventional ethanol plant) is located at terminus 202 of a network of liquid biomass extract pipelines 214. Input of liquid biomass extract into the network is provided by one or more individual liquid biomass extract production sites. In the example shown in FIG. 2, five individual liquid biomass extract production sites 204, 206, 208, 210, and 212 provide extract input to pipelines 214. The number of individual liquid biomass extract production sites can be any number. In some embodiments, there can be between about 1 and about 100 sites that input the same network of pipelines. In some embodiments, there are at least two liquid biomass production sites. In some embodiments, there are at least 10, 20, 30, 40, 50, 60, 70, 80, or 90 individual production sites. There can also be more than 100 individual liquid biomass extract production sites that input extract into the same network of pipelines. In some embodiments, there are at least 150, 200, 300, 400, 500, 750, 1000, 2000, 5000 or more individual liquid biomass extract production sites that input the same network of pipelines.

Each individual liquid biomass extract production site includes a biomass source (e.g., a field wherein a biomass plant source is grown and harvested), an atmospherically controlled chamber wherein green biomass can be saccharified or saccharified and fermented to provide liquefied biomass, and an extractor for removing at least a portion of the liquids in the liquefied biomass. Thus, referring again to FIG. 2, individual liquid biomass production site 212 includes biomass source 212', atmospherically controlled chamber 212", extractor 212''', and pipeline inlet 212''''. As will be understood by one of skill in the art, the individual liquid biomass production sites can include additional components, as necessary for harvesting and liquefying the biomass, extracting the liquefied biomass, and pumping the liquid biomass extract, including, but not limited to, silage choppers; hoppers, conveyors, or other suitable devices for feeding biomass into the atmospherically controlled chamber; harvesting equipment for harvesting the biomass; and pumping equipment to pump the liquid biomass extract into the pipeline. Other components can include spraying devices for adding inoculant to the biomass, liquid storage containers for temporary liquid biomass extract storage, and drying and processing equipment for handling the residual solids fraction from the liquefied biomass.

A particular pipeline, originating from an individual liquid biomass production site can feed directly to terminus 202 or can join a pipeline originating from one or more additional liquid biomass production site. Thus, the network of pipelines can include one or more branch points, where pipelines originating from individual sites or groups of sites feed into other portions of the pipeline network. For example, in FIG. 2, the pipeline originating from site 208 joins the pipeline originating from site 206 at branch point 216. The pipeline from branch point 216 carrying liquid biomass extract from sites 206 and 208 joins the pipeline originating at site 204 at branch point 218. Depending on the volume of liquid biomass extract being carried at any particular point in the network, the diameter of the pipeline can vary. The pipeline network can further include one or more pumping stations to facilitate flow of the liquid biomass extract.

In some embodiments, terminus 202 can include the termini of several individual pipelines in the network. Liquid biomass extract can be fed into treatment facility 200 as it arrives or can be stored for a time and fed into treatment facility 200 in batches.

In some embodiments, the system can be used to pipe slurry comprising partially hydrolyzed biomass (e.g., partially hydrolyzed green biomass). Thus, in some embodiments, the presently disclosed subject matter provides a system for converting biomass to a biofuel, the system comprising:

a treatment facility for processing biomass slurry; and a network comprising one or more pipelines for providing biomass slurry to the treatment facility from one or more remotely located slurry production sites, wherein each of the remotely located slurry production sites comprises a biomass source, an atmospherically controlled chamber, and a pipeline inlet providing access to the one or more pipelines. In some embodiments, each of the one or more remotely located slurry production sites is at least about 8 kilometers from the treatment facility. Each of the individual slurry production sites can comprise a grinder or mixer for preparing biomass slurry from biomass following partial saccharification and/or alcohol fermentation of the biomass in an atmospherically controlled chamber.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Corn Hybrid Biomass

The biomass content of various corn plant segment samples was estimated based on weight. As indicated in Table 1, below, segment samples were obtained from ten different corn hybrids, including: CROPLAN® 421TS (Land O'Lakes, Inc.; St. Paul, Minn., United States of America); DEKALB® DKC52-47 and DEKALB® DKC63-39 (DeKalb Genetics Corp.; DeKalb, Ill., United States of America); NK® N60-B4, NK® N70-C7; GARST® 8487, and GOLDEN HARVEST® L9H53 (Syngenta Participations AG; Basel, Switzerland); Mycogen 2C597 (Dow AgroSciences, LLC; Indianapolis, Ind., United States of America); Renk RK670RR (Renk Seed; Sun Prairie, Wis., United States of America), and PIONEER® 33T56 (Pioneer Hi-Bred International, Inc.; Johnston, Iowa, United States of America). The corn plants were harvested after reaching physiological maturity at a cut height of about 15 centimeters and dried for 40 days prior to analysis. The plants were segmented into samples and weighed (in grams) as indicated in Table 2. The average (Ave) of the ten hybrid samples is also provided for each segment type.

TABLE 1

Corn Sample Growing Conditions.

| Sample # | Nearest Town | State | Row Width (cm) | Plant Spacing (cm) | Brand | Hybrid |
|---|---|---|---|---|---|---|
| 1 | Lake Crystal | MN | 76.2 | 30.5 | CROPLAN ® | 421TS |
| 2 | Madelia | IA | 76.2 | 35.6 | DEKALB ® | DKC52-47 |
| 3 | Sully | IA | 76.2 | 30.5 | NK ® | N60-B4 |
| 4 | Knoxville | IA | 96.5 | 33.0 | GARST ® | 8487 |
| 5 | Fairview | SD | 76.2 | 35.6 | Mycogen | 2C597 |
| 6 | Waterbury | NE | 76.2 | 38.1 | DEKALB ® | DKC63-39 |
| 7 | Ravenswood | MO | 76.2 | 45.7 | NK ® | N70-C7 |
| 8 | Jackson | NE | 76.2 | 27.9 | GOLDEN HARVEST ® | L9H53 |
| 9 | Canton | SD | 96.5 | 40.6 | Renk | RK670RR |
| 10 | Wilcox | MO | 76.2 | 35.6 | PIONEER ® | 33T56 |

TABLE 2

Corn Biomass Segment Weight (in grams).

| Sample | Moisture (%) | Grain Weight | Cob Weight | Weight Leaves, Husk, and Silk | Total Stalk Weight | Total Weight | Total Biomass Weight (no grain) |
|---|---|---|---|---|---|---|---|
| 1 | 7.2 | 130.4 | 17.0 | 51.0 | 45.4 | 243.8 | 113.4 |
| 2 | 7.8 | 249.5 | 28.4 | 90.7 | 62.4 | 430.9 | 181.4 |
| 3 | 8.0 | 195.6 | 22.7 | 51.0 | 48.2 | 317.5 | 121.9 |
| 4 | 10.1 | 277.8 | 34.0 | 102.1 | 96.4 | 510.3 | 232.5 |
| 5 | 7.7 | 192.8 | 22.7 | 73.7 | 85.1 | 374.2 | 181.4 |
| 6 | 9.8 | 255.1 | 34.0 | 102.1 | 73.7 | 464.9 | 209.8 |
| 7 | 6.3 | 170.1 | 22.7 | 62.4 | 68.0 | 323.2 | 153.1 |
| 8 | 9.7 | 141.8 | 17.0 | 51.0 | 39.7 | 249.5 | 107.7 |

TABLE 2-continued

Corn Biomass Segment Weight (in grams).

| Sample | Moisture (%) | Grain Weight | Cob Weight | Weight Leaves, Husk, and Silk | Total Stalk Weight | Total Weight | Total Biomass Weight (no grain) |
|---|---|---|---|---|---|---|---|
| 9 | 5.9 | 181.4 | 22.7 | 73.7 | 68.0 | 345.9 | 164.4 |
| 10 | 6.5 | 107.7 | 17.0 | 51.0 | 45.4 | 221.1 | 113.4 |
| Ave | 7.9 | 190.2 | 23.8 | 70.9 | 63.2 | 348.1 | 157.9 |

The weight of the stalk (in grams) above and below the ear is compared to the length of the stalk (in centimeters) above and below the ear in Table 3. In each of the hybrids tested, the stalk portion below the ear weighed more than the stalk portion above the ear although all samples had less stalk length below the ear.

TABLE 3

Comparison of Stalk Weight (grams) and Length (centimeters) in Above and Below Ear Stalk Samples.

| Sample | Stalk Weight Above Ear | Stalk Weight Below Ear | Stalk Length Above Ear | Stalk Length Below Ear |
|---|---|---|---|---|
| 1 | 11.3 | 34.0 | 141.6 | 71.1 |
| 2 | 11.3 | 51.0 | 139.7 | 102.9 |
| 3 | 17.0 | 31.2 | 149.9 | 92.7 |
| 4 | 39.7 | 56.7 | 179.1 | 95.9 |
| 5 | 11.3 | 73.7 | 127.0 | 115.6 |
| 6 | 22.7 | 51.0 | 172.7 | 89.5 |
| 7 | 28.4 | 39.7 | 212.1 | 95.9 |
| 8 | 11.3 | 28.4 | 128.3 | 76.2 |
| 9 | 17.0 | 51.0 | 116.2 | 80.0 |
| 10 | 11.3 | 34.0 | 161.3 | 76.2 |
| Average | 18.1 | 45.1 | 152.8 | 89.6 |

Example 2

Dry Matter Analysis

For further chemical analysis, three segmented biomass samples were prepared from one individual corn plant of each of the following three corn hybrids described in Table 1: GARST® 8487, NK® N70-C7, and GOLDEN HARVEST® L9H53 (Syngenta Participations AG, Basel, Switzerland). The three types of segmented sample were: corn fodder (leaves/husk/silk), corn fodder (total stalks/tassel), and grain.

Chemical analysis of the samples was performed at the Oscar E. Olson Biochemistry Laboratories, South Dakota State University, Brookings, S. Dak. Starch, oil and crude protein percentages in the grain samples were determined via NIRS. The crude protein, oil and starch contents of the grain samples are given in Table 4. Table 5 provides data from the analysis of the leaves/husk/silk samples. Table 6 provides data from the analysis of the total stalk/tassel samples. All data is provided as a % of the dry matter. As described in Example 1, the plants were harvested at a 15 centimeter cut height, thus the analysis reflects the chemical content of plant material generally included in harvested biomass, not the total available aerial biomass.

TABLE 4

Corn Grain NIRS Analysis (% DM).

| Sample | Crude Protein | Oil | Starch |
|---|---|---|---|
| GARST® 8487 | 9.9 | 3.32 | 70.6 |
| NK® N70-C7 | 8.6 | 4.77 | 67.1 |
| GOLDEN HARVEST® L9H53 | 7.2 | 3.88 | 70.4 |
| Average | 8.57 | 3.99 | 69.37 |

TABLE 5

Corn Fodder (Leaves/Silk/Husk) Chemical Analysis (% DM).

| Sample | Crude Protein[a] | Crude Fat[b] | Ash | ADF[c] | NDF[d] | Lignin-sulfuric acid | TDN[e] |
|---|---|---|---|---|---|---|---|
| GARST® 8487 | 9.56 | 1.71 | 9.46 | 38.8 | 66.8 | 3.21 | 58.5 |
| NK® N70-C7 | 5.47 | 0.91 | 7.88 | 49.5 | 78.0 | 4.88 | 53.0 |
| GOLDEN HARVEST® L9H53 | 4.64 | 1.27 | 10.2 | 46.3 | 75.4 | 3.72 | 54.2 |
| Average | 6.56 | 1.30 | 9.18 | 44.87 | 73.40 | 3.94 | 55.23 |

[a] combustion
[b] diethyl ether extract
[c] acid detergent fiber
[d] neutral detergent fiber
[e] total digestible nutrients

TABLE 6

Corn Fodder (Stalk/Tassel) Chemical Analysis (% DM).

| Sample | Crude Protein[a] | Crude Fat[b] | Ash | ADF[c] | NDF[d] | Lignin-sulfuric acid | TDN[e] |
|---|---|---|---|---|---|---|---|
| GARST® 8487 | 4.02 | 0.53 | 2.96 | 37.8 | 57.2 | 4.82 | 63.3 |
| NK® N70-C7 | 4.0 | 0.62 | 5.72 | 56.8 | 81.1 | 9.3 | 46.8 |
| GOLDEN HARVEST® L9H53 | 3.49 | 1.99 | 5.61 | 41.3 | 64.3 | 5.49 | 59.5 |
| Average | 3.84 | 1.05 | 4.76 | 45.30 | 67.53 | 6.54 | 56.53 |

[a] combustion
[b] diethyl ether extract
[c] acid detergent fiber
[d] neutral detergent fiber
[e] total digestible nutrients The percentages of crude protein, crude fat, and NDF (or starch from the grain samples) were averaged from the samples of all three hybrids. The average data from each of the three types of segmented sample is provided in Table 7.

The average protein, fat and NDF/starch percentages of the entire plant (minus the cob) is also provided. Although the stalk/tassel portion had somewhat less NDF/starch, it had significantly lower non-fermentable crude protein and crude fat.

TABLE 7

Average Corn Protein, Fat and NDR or Starch (% DM).

| Corn Segment | Crude Protein[a] | Crude Fat[b] | NDF/Starch[f] |
|---|---|---|---|
| Average Fodder (leaves, silk, husk) | 6.56 | 1.30 | 73.4 |
| Average Fodder (stalk, tassel) | 3.84 | 1.05 | 67.53 |
| Average grain | 8.57 | 3.99 | 69.37 |
| Average whole plant (minus cob) | 6.32 | 2.11 | 70.1 |

[a]combustion
[b]diethyl ether extract
[f]neutral detergent fiber % average of fodder samples, starch % average of grain samples The non-fermentable chemical content of the two fodder segments is compared in Table 8. The data indicates that the leaves/silk/husk portion of the corn plants contain a higher percentage of non-fermentable material than do the stalk/tassel portions.

TABLE 8

Non-Fermentable Corn Content (% DM)

| | Ash | Lignin-sulfuric acid | Crude Protein[a] | Crude Fat[b] | Total Non-fermentables |
|---|---|---|---|---|---|
| Average Fodder (leaves, silk, husk) | 9.18 | 3.94 | 6.56 | 1.3 | 20.98 |
| Average Fodder (stalk, tassel) | 4.76 | 6.54 | 3.84 | 1.05 | 16.19 |
| Average whole plant (minus cob and grain) | 6.97 | 5.24 | 5.2 | 1.18 | 18.59 |

[a]combustion
[b]diethyl ether extract

Example 3

Biomass Sugar Content and Harvest Timing

Harvest timing can affect the volume and type of sugars present in biomass. As shown in Table 9, sugar levels differ between crops and within the same crop harvested at different times or grown under different conditions. In the biomass samples described in Table 9, some forages harvested 58 days after planting had much less sucrose, fructose and glucose than the same crops harvested and analyzed after 102 days. Subsequently, the crops harvested after 132 days of growth were subjected to twenty-one days of drying post harvest in mesh poly bags to allow free flow of air. Sugar composition significantly changed with maturity and drying. For example sucrose levels were highest after 102 days of growth, except when ears were mechanically removed from whole-plant corn. Testing after 132 days and drying showed decreased sucrose, but increased fructose and glucose levels. Variation in sugar levels and sugar types were observed between types of forage and were affected by maturity. Sugar levels can be used to determine harvest timing and the choice of inoculant type (e.g., enzyme identity and amount).

TABLE 9

Fermentable Sugar Analysis of Various Forages[a] Based on Harvest Timing

| Forage Type | Days Planting to Harvest | Sucrose %[b] | Fructose %[b] | Glucose %[b] | Lactose %[b] | Maltose %[b] |
|---|---|---|---|---|---|---|
| Millex 32-hybrid pearl millet | 58 | N.D | N.D. | N.D. | N.D. | N.D. |
| Millex 32-hybrid pearl millet | 102 | 2.28 | 3.11 | 1.63 | N.D. | N.D. |
| Millex 32-hybrid pearl millet | 132 | 0.362 | 5.64 | 4.96 | N.D. | N.D. |
| Trudan headless-Sudangrass | 58 | 3.69 | 1.47 | 1.76 | N.D. | N.D. |
| Trudan headless-Sudangrass | 102 | 9.27 | 2.43 | 2.22 | N.D. | N.D. |
| Trudan headless-Sudangrass | 132 | 7.80 | 3.99 | 4.29 | N.D. | N.D. |
| N40T corn-whole plant | 102 | 8.77 | 1.67 | 1.79 | N.D. | N.D. |
| N40T corn-whole plant | 132 | 0.367 | 0.901 | 1.07 | N.D. | N.D. |
| N40T corn-ear removed before pollination | 102 | 17.8 | 4.01 | 4.06 | N.D. | N.D. |
| N40T corn-ear removed before pollination | 118 | 21.0 | 3.08 | 3.07 | N.D. | N.D. |
| N40T corn-ear removed before pollination | 132 | N.D. | 7.62 | 7.65 | N.D. | N.D. |

TABLE 9-continued

Fermentable Sugar Analysis of Various Forages[a] Based on Harvest Timing

| Forage Type | Days Planting to Harvest | Sucrose %[b] | Fructose %[b] | Glucose %[b] | Lactose %[b] | Maltose %[b] |
|---|---|---|---|---|---|---|
| Derry Forage Soybean | 102 | 0.591 | 5.04 | N.D. | N.D. | N.D. |
| Derry Forage Soybean | 132 | N.D. | 1.36 | 1.31 | N.D. | N.D. |
| HiKane II-forage sorghum | 102 | 18.80 | 3.34 | 3.36 | N.D. | N.D. |
| HiKane II-forage sorghum | 132 | 7.06 | 4.41 | 5.31 | N.D. | N.D. |
| Sucrosorgo 405-forage sorghum | 102 | 10.80 | 4.55 | 4.06 | N.D. | N.D. |
| Sucrosorgo 405-forage sorghum | 132 | 9.44 | 6.58 | 6.69 | N.D. | N.D. |
| Sordan headless-sorghum × Sudangrass hybrid | 102 | 6.47 | 2.59 | 2.60 | N.D. | N.D. |
| Sordan headless-sorghum × Sudangrass hybrid | 132 | 5.85 | 4.84 | 5.53 | N.D. | N.D. |

N.D. means none detected.
Millex 32, Trudan, HiKane II, and Sucrosorgo 405 hybrids are available from Sorghum Partners, Inc. (New Deal, Texas, United States of America); N40T corn hybrid is available from NK ® Brand (Syngenta Participations AG; Basel, Switzerland); the Derry forage soybean was developed by the USDA-ARS (Beltsville, Maryland, United States of America). Sugar analysis of the samples was performed at the Oscar E. Olson Biochemistry Laboratories, South Dakota State University, Brookings, South Dakota, United States of America.
[a]six inch cut height
[b]% on a dry weight basis Example 4

Preparation and Extraction of Liquefied Biomass

Biomass moisture content can be monitored so that the biomass is harvested when it has a moisture content of at least about 70%. If desired, the biomass can also be monitored during growth so that harvesting can occur when a particular sugar content is present. For example, the biomass can be harvested when the sugar content (e.g., sucrose, fructose, glucose, and/or combinations thereof) is at least about 10% (on a dry weight basis). Drought or frost conditions can be taken into consideration, as such conditions can affect levels of endogenous microbes (which can affect alcohol fermentation) and/or moisture levels. Harvesting conditions can be chosen such that the biomass is not allowed to dry more than about 5% between the field and the silo. If possible, an ambient harvest temperature of about 21° C. or more, with minimal wind, can provide suitable initial heat within the atmospherically controlled chamber, while at the same time keeping the moisture loss of the biomass to a minimum. Generally, manure application to the biomass-containing field should be halted at least about 30 days prior to harvest to minimize the presence of non-beneficial microbes.

While the biomass can comprise any lignocellulose-containing plant matter, one exemplary biomass material is whole plant corn. If desired, the corn plants can comprise a transgenic corn hybrid that produces an amylase enzyme. The corn plants can be harvested early in the R3 stage (i.e., the early "milk stage," which begins about 20 days after silking). Kernel pollination in the corn plant can be blocked through mechanical, chemical or genetic means, to increase sugar content.

Using a commercial silage chopper, the whole corn plant aerial biomass is cut about 15 centimeters above ground, and the corn is chopped to approximately 0.3 to 0.35 cm theoretical cut length (TLC). The chopped corn is then loaded into an atmospherically controlled chamber, such as an enameled steel silo (i.e., a "glass-lined" silo). Suitable silo sizes include, but are not limited to, about 6.1 m×32.3 m or about 7.6 m×32.3 m. Suitable silos and silo filling/emptying equipment is commercially available from Nebraska Harvestore Systems, Inc. (Norfolk, Nebr., United States of America), and Vitkovice Power Engineering, Ltd. (Ostrava, Czech Republic). Pneumatic or conveyance systems can be used to load silos to minimize biomass drying. To maximize biomass consistency, compaction, and uniformity of enzymatic conversion and/or microbial fermentation, the silo should be filled and sealed rapidly (e.g., within about 12 hours). Further, the time elapsing between the harvesting of a particular plant and its being loaded into the silo should be minimized. If possible, the plant is chopped and loaded into the silo within about 20 minutes of harvest from the field.

When used, inoculant can be sprayed onto the chopped biomass as a water solution either in the chopper or as the biomass is being loaded into the silo. The inoculant can include commercially available enzymes, including, but not limited to, MULTIFECT™ or MUTIFECT™ A40 (Genencor International, Inc., Palo Alto, Calif., United States of America); SAFIZYM™FI300 (LeSaffre et Campagnie Corporation, Marcq en Baroeul, France); and ENZENCO® preparations (Enzyme Development Corp., New York, N.Y., United States of America). The inoculant can include commercially available yeasts from companies, including, but not limited to, Lallemand Ethanol Technology (Rexdale, Ontario, Canada), Taurus Energy (Lund, Sweden), and Fermentis (S.I. LeSaffre, Marcq en Baroeul, France). The inoculant can include one or more bacteria, such as a cellulase-producing bacteria (e.g., *Trichoderma reesei*) or a bacteria (e.g., *Z. mobilis*) that can ferment glucose or xylose to ethanol. Suitable bacteria include, but are not limited to, ethanol producing bacteria from Mascoma Corporation (Boston, Mass., United States of America). Other inoculant components can include, but are not limited to, microbial nutrients, oxygen-depleting agents, pH-adjusting agents, and the like.

The silo can be continuously filled to maximize biomass compaction. Compaction, TLC, and moisture content of the biomass can affect oxygen minimization in the silo. The bulk density of the biomass will be highest at the bottom of the silo and will contain the oldest chopped biomass. Carbon dioxide gas can be injected at various silo heights, for instance, above the biomass level, to decrease the concentration of air surrounding the biomass, thereby minimizing the oxygen concentration.

WSC can be monitored at any time during saccharification. For example, WSC can be monitored on an hourly basis from liquefying biomass in the bottom meter of the silo so that extraction timing maximizes extraction of WSC and/or alcohols. In particular, monitoring can be used to time extraction to occur before potential microbial wasting and/or conversion of WSC to organic acid by-products. Both escaping air and liquid seepage can also be monitored to detect changes in the biomass. In addition, temperature and biomass density can be monitored. Generally, the temperatures produced by the liquefying process (e.g., by piling of the green biomass and/or by microbial activity, in the absence of added heat) are expected to be between about 26° C. and about 49° C. In some cases, the temperature increase caused by the piling of the green biomass will be between about 9 and 12° C.

WSC can be measured using previously published methods. See, e.g., Murphy et al., *Bioresource Technology*, 98, 3106-3111 (2007); and Philipp et al., Biomass and Bioenergy, 31(7), 492-496 (2007). Fermentation monitoring can be accomplished via any suitable means, such as, but not limited to, Fourier Transform infrared (FTIR) methods. While results can vary depending upon the conditions in the silo (e.g., temperature, moisture, oxygen level, container size, biomass density, microbial/enzymatic activity, etc.) and upon the content of the incoming biomass (e.g, moisture, sugar content, etc.), total WSC can peak between about 20 and 72 hours (e.g., between about 24 and about 36 hours) after the silo is filled. Serial extraction of portions of the liquefied biomass can begin when the WSC peaks or shortly before (e.g., within about 1, 2, 3, 4, 5, or 6 hours before).

Serial extraction can be accomplished by unloading the liquefied biomass from the bottom of the silo or other atmospherically controlled chamber. Suitable unloading equipment includes the Harvestore LX 400 Silo Unloader (Nebraska Harvestore Systems, Inc.; Norfolk, Nebr., United States of America), or any other commercial unloader that can unload biomass at a rate compatible with the rate of subsequent extraction of the biomass. Extraction of the biomass can be performed using a commercial multiple steel roller or belt press, such as those used in sugar cane processing and/or pressure belt filter presses (e.g., the Pneumapress®; Pneumapress Filter Corp., Richmond, Calif., United States of America). Ideally, the press extracts the liquefied biomass using minimal wash water.

Following extraction of the liquefied biomass, the liquid extract can be assayed to determine sugar, alcohol, and WSC content. The liquefied biomass can also be assayed to determine the presence and/or amounts of various nutrients (e.g., microbial nutrients, such as nitrogen- and/or phosphorous-containing compounds that could be useful fertilizer components) and to determine levels of remaining biomass-processing biocatalysts. If desired, the liquid biomass extract can be treated to adjust the pH for storage or transport. Further, the liquid biomass extract can be treated with additional biomass-processing biocatalysts to control viscosity. Alternatively, it can be desirable to treat the liquefied biomass with antibacterials (e.g., to prevent acid fermentation of available sugars).

It will be understood that various details of the presently disclosed subject matter may be changed without departing from the scope of the presently disclosed subject matter. Furthermore, the foregoing description is for the purpose of illustration only, and not for the purpose of limitation.

The invention claimed is:

1. A process for converting biomass to a liquid biomass extract comprising fermentable sugars; the process comprising:
    providing biomass, wherein providing the biomass comprises harvesting a plant material, wherein the harvesting is timed to provide a freshly harvested, green, whole plant material comprising a moisture content of between about 70% and about 95%, wherein the between about 70% and the about 95% moisture come from the biomass;
    placing the biomass into an atmospherically controlled chamber for a period of time and under suitable conditions to effect saccharification of the biomass, alcohol fermentation of the biomass, or a combination thereof, thereby providing a liquefied biomass, wherein the liquefied biomass comprises residual solids, biomass-derived water, and water-soluble products, the water soluble products comprising fermentable sugars or fermentable sugars and an alcohol; and
    serially extracting the liquefied biomass, wherein serially extracting the liquefied biomass comprises:
    removing a first portion of the liquefied biomass from the chamber;
    collecting at least a portion of the biomass-derived water and water soluble products from the first portion of the liquefied biomass; and
    repeating the removing and collecting for one or more additional portions of the liquefied biomass;
    thereby providing a liquid biomass extract and a residual solids fraction wherein the plant material is derived from a plant selected from one or more of the group consisting of maize, soybean, millet, milo, rye, wheat, triticale, oats, barley, rice, sudangrass, switchgrass, *Miscanthus*, alfalfa, cotton, sisal, hemp, jute, turf grass, rape, sunflower, willow, eucalyptus, poplar, pine, willow, tobacco, clover, bamboo, flax, pea, radish, turnip, potato, sweet potato, cassava, taro, beet, sugar beet, and canola.

2. The process of claim 1, wherein providing the biomass further comprises chopping the biomass.

3. The process of claim 2, wherein the chopping comprises chopping the biomass to a theoretical length of cut (TLC) between about 0.3 and about 1.3 centimeters.

4. The process of claim 1, wherein the suitable conditions further comprise providing an inoculant comprising one or more biomass-processing biocatalyst.

5. The process of claim 4, wherein the inoculant is added to the biomass prior to or during the placing of the biomass into the atmospherically controlled chamber.

6. The process of claim 4, wherein the biomass-processing biocatalyst comprises one or more of a lignocellulose-processing enzyme and an alcohol-producing microbe.

7. The process of claim 1, further comprising monitoring contents of the atmospherically controlled chamber at one or more locations in the chamber to determine one or more of the group consisting of pH, temperature, oxygen gas content, escaping gases, microbial activity, enzymatic activity, % dry matter (DM) conversion, % of theoretical sugars converted, fermentable sugars concentration, alcohol concentration, plant material-derived acid concentration, and microbial nutrient concentration.

8. The process of claim 1, wherein the biomass comprises one or more of the group consisting of whole plant corn, and soybean forage.

9. The process of claim 8, wherein the transgenic plant comprises one or more lignocellulose-processing enzyme.

10. The process of claim 1, wherein the harvesting is timed to provide a plant material comprising a moisture content of about 75% or more.

11. The process of claim 10, wherein the lignocellulose-processing enzyme is an amylase.

12. The process of claim 1, wherein the biomass comprises plant material selected based on one or more characteristic of the group consisting of sugar content, cellulose content, lignin content, cost, growing season, drought resistance, disease resistance, individual plant size, and tonnage.

13. The process of claim 12, wherein the biomass comprises plant material from a male-sterile, tropical hybrid corn plant.

14. The process of claim 1, wherein at least a portion of the plant material is derived from a transgenic plant.

15. The process of claim 14, wherein the period of time is from about 24 hours to about 72 hours.

16. The process of claim 1, wherein the atmospherically controlled chamber is an upright silo.

17. The process of claim 1, wherein the period of time is from about 20 hours to about 21 days.

18. The process of claim 17, further comprising transporting the liquid biomass extract to a second location; and treating the liquid biomass extract to provide a biofuel.

19. The process of claim 18, wherein treating the liquid biomass extract comprises one or more of fermenting fermentable sugars in the liquid biomass extract and purifying the liquid biomass extract to provide a purified alcohol.

20. The process of claim 19, wherein the treating further comprises saccharifying water soluble carbohydrates in the liquid biomass extract.

21. The process of claim 1, wherein the collecting comprises one or more of centrifuging, pressing, and decanting.

22. The process of claim 1, wherein the liquid biomass extract comprises water soluble products and at least about 80% of the biomass-derived water from the first portion and the one or more additional portions of the liquefied biomass, and the residual solids fraction comprises the residual solids and about 20% of the biomass-derived water from the first portion and the one or more additional portions of the liquefied biomass.

23. The process of claim 1, wherein the plant material is harvested at a first location and the atmospherically controlled chamber is at a location at or in close proximity to the first location.

24. The process of claim 1, further comprising treating the residual solids fraction to provide one or more co-products selected from the group consisting of an animal feed, a fertilizer, methanol, and a boiler fuel.

25. The process of claim 1, further comprising collecting the biomass-derived water from the liquid biomass extract and using the biomass-derived water for one or more of irrigating a biomass plant material prior to harvesting; diluting the biomass or liquid biomass extract for saccharification, fermentation, or saccharification and fermentation; processing a residual solids fraction; and distilling a biofuel.

* * * * *